US008197809B2

(12) United States Patent
Park et al.

(10) Patent No.: US 8,197,809 B2
(45) Date of Patent: Jun. 12, 2012

(54) CD9-SPECIFIC HUMAN ANTIBODIES

(75) Inventors: Young Woo Park, Daejeon (KR); So-Young Choi, Daejoen (KR); Ji Hyun Park, Gyeongsangnam-do (KR); Jung Yu, Daejeon (KR); Eun-Jung Song, Daejeon (KR); Sungsub Kim, Daejeon (KR); Myeoung Hee Jang, Daejeon (KR); Mi-Ju Park, Daejeon (KR); Je-Ho Lee, Seoul (KR); Jae Ryoung Hwang, Seoul (KR)

(73) Assignees: Korea Research Institute of Bioscience and Biotechnology (KR); Sungkyunkwan University Foundation for Corporate Collaboration (KR)

( * ) Notice: Subject to any disclaimer, the term of this patent is extended or adjusted under 35 U.S.C. 154(b) by 311 days.

(21) Appl. No.: 12/523,516

(22) PCT Filed: Nov. 24, 2008

(86) PCT No.: PCT/KR2008/006913
§ 371 (c)(1),
(2), (4) Date: Jul. 16, 2009

(87) PCT Pub. No.: WO2009/157623
PCT Pub. Date: Dec. 30, 2009

(65) Prior Publication Data
US 2011/0195027 A1 Aug. 11, 2011

(30) Foreign Application Priority Data
Jun. 25, 2008 (KR) .................. 10-2008-0059981

(51) Int. Cl.
C07K 16/00 (2006.01)
G01N 33/53 (2006.01)
A61K 39/395 (2006.01)

(52) U.S. Cl. ............... 424/130.1; 424/133.1; 424/143.1; 424/155.1; 435/7.1

(58) Field of Classification Search .................. None
See application file for complete search history.

(56) References Cited

U.S. PATENT DOCUMENTS
5,859,205 A * 1/1999 Adair et al. ................ 530/387.3

OTHER PUBLICATIONS

Brown et al. "Tolerance to Single, but not multiple, amino acid replacements in antibody VH CDR2" J. Immuno, 1996, 156: pp. 3285-3291.*
Eduardo Padlan, "Anatomy of the antibody molecule" Molecular Immun. 31(3) (1994), pp. 169-217.*
William E. Paul, M.D. "Fundamental Immunology" 3rd Edition, 1993, 292-295.*
Rudikoff et al. "Single amino acid substitution altering antigen-binding specificity" Proc. Natl. Acad. Sci. USA, 79 (Mar. 1982), pp. 1979-1983.*
Vajdos et al. "Comprehensive functional maps of the antigen-binding site of an anti-ErbB2 antibody obtained with shotgun scanning mutagenesis" J. Mol. Biol. (2002) 320, pp. 415-428.*
Cook et al., "Identification of CD9 extracellular domains important in regulation of CHO cell adhesion to fibronectin and fibronectin pericellular matrix assembly," Blood, 100(13):4502-4511 (Dec. 15, 2002).
Drapkin et al., "Expression of Candidate Tumor Markers in Ovarian Carcinoma and Benign Ovary: Evidence for a Link Between Epithelial Phenotype and Neoplasia," Human Pathology, 35(8):1014-1021 (Aug. 2004).
Erovic et al., "Motility-related protein-1/CD9 expression in head and neck squamous cell carcinoma," Head & Neck, 25:848-857 (Oct. 2003).
Funakoshi et al., "Expression of tetraspanins in human lung cancer cells: frequent downregulation of CD9 and its contribution to cell motility in small cell lung cancer," Oncogene, 22:674-687 (2003).
Higashiyama et al., "Reduced Motility Related Protein-1 (MRP-1/CD9) Gene Expression as a Factor of Poor Prognosis in Non-Small Cell Lung Cancer," Cancer Research, 55:6040-6044 (Dec. 15, 1995).
Houle et al., "Loss of Expression and Altered Localization of KAI1 and CD9 Protein Are Associated with Epithelial Ovarian Cancer Progression," Gynecologic Oncology, 86:69-78 (2002).
Le Naour et al., "Profiling of the Tetraspanin Web of Human Colon Cancer Cells," Molecular & Cellular Proteomics 5.5, 5:845-857 (2006).
Masellis-Smith and Shaw "CD9-Regulated Adhesion: Anti-CD9 Monoclonal Antibody Induce Pre-B Cell Adhesion to Bone Marrow Fibroblasts Through de Novo Recognition of Fibronectin," Journal of Immunology, 152:2768-2777 (1994).
Miyake et al., "Motility Related Protein 1 (MRP-1/CD9) Expression: Inverse Correlation with Metastases in Breast Cancer," Cancer Research, 55:4127-4131 (Sep. 15, 1995).
Mori et al., "Motility Related Protein 1 (MRP1/CD9) Expression in Colon Cancer," Clinical Cancer Research, 4:1507-1510 (Jun. 1998).
Peters et al., "Comparative Gene Expression Analysis of Ovarian Carcinoma and Normal Ovarian Epithelium by Serial Analysis of Gene Expression," Cancer Epidemiology, Biomarkers and Prevention, 14(7):1717-1723 (Jul. 2005).
Radford et al., "CD63 Associates with Transmembrane 4 Superfamily Members, CD9 and CD81, and with 1 Integrins in Human Melanoma," Biochemical and Biophysical Research Communications, 222:13-18, Article No. 0690 (1996).
Takeda et al., "Adenoviral Transduction of MRP-1ICD9 and KAI1/CD82 Inhibits Lymph Node Metastasis in Orthotopic Lung Cancer Model," Cancer Research, 67(4):1744-1749 (Feb. 15, 2007).

* cited by examiner

Primary Examiner — Maher Haddad
Assistant Examiner — James Rogers
(74) Attorney, Agent, or Firm — Klarquist Sparkman, LLP.

(57) ABSTRACT

The present invention relates to a CD9-specific human antibody, more precisely a CD9-specific human antibody composed of human derived CD9-specific complementarity determining region (CDR) and framework region (FR). The human antibody of the present invention recognizes CD9 extracellular loop 2 domain (CD9-ECL2) as an epitope and thereby strongly binding thereto. The human antibody of the present invention also has CD9 antigen neutralizing effect and at the same time inhibiting effect on tumor cell lines. Therefore, it can be effectively used for the prevention and treatment of cancer overexpressing CD9.

7 Claims, 15 Drawing Sheets

[Fig. 1]
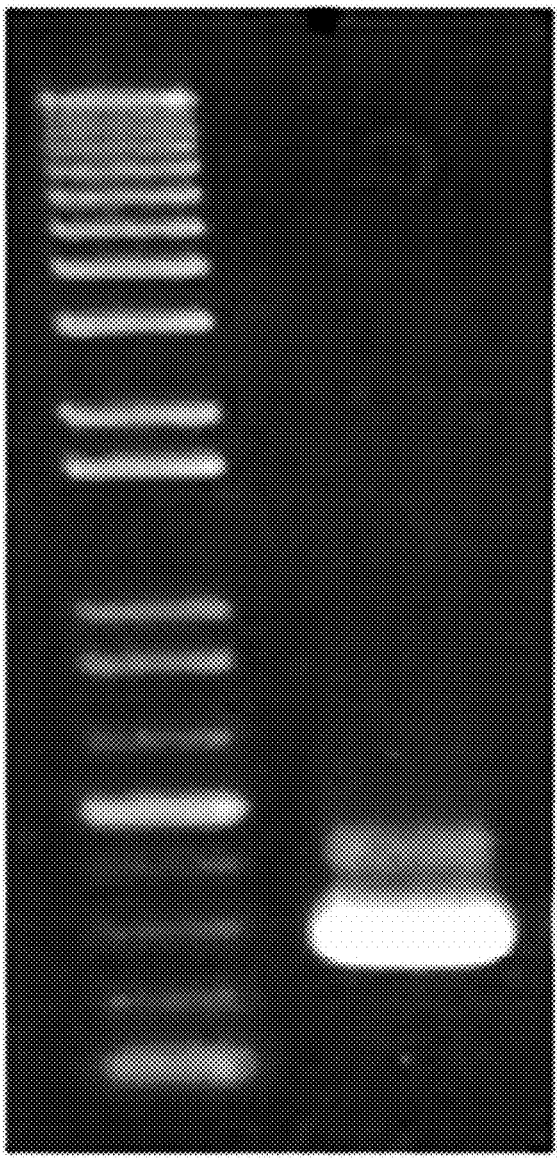

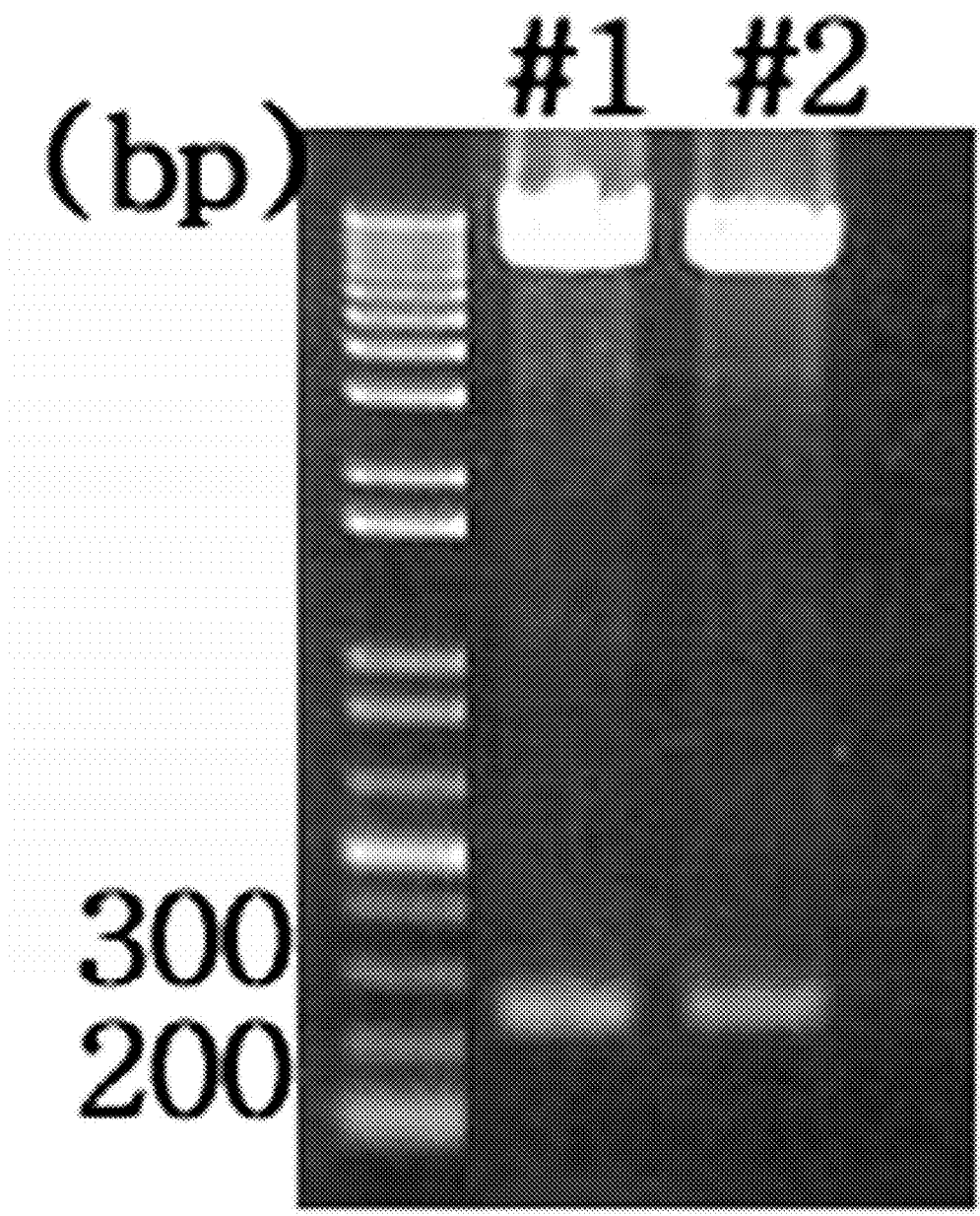
[Fig. 2]

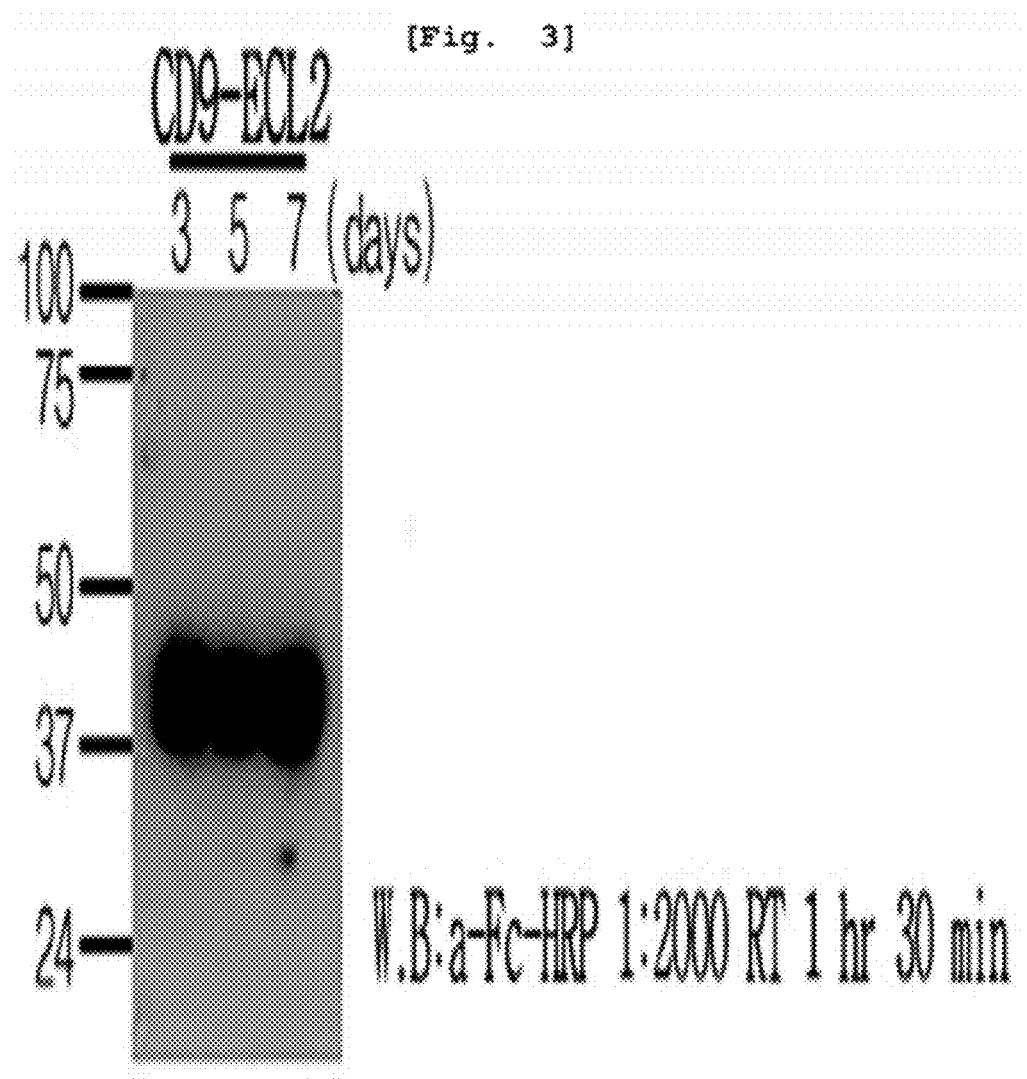

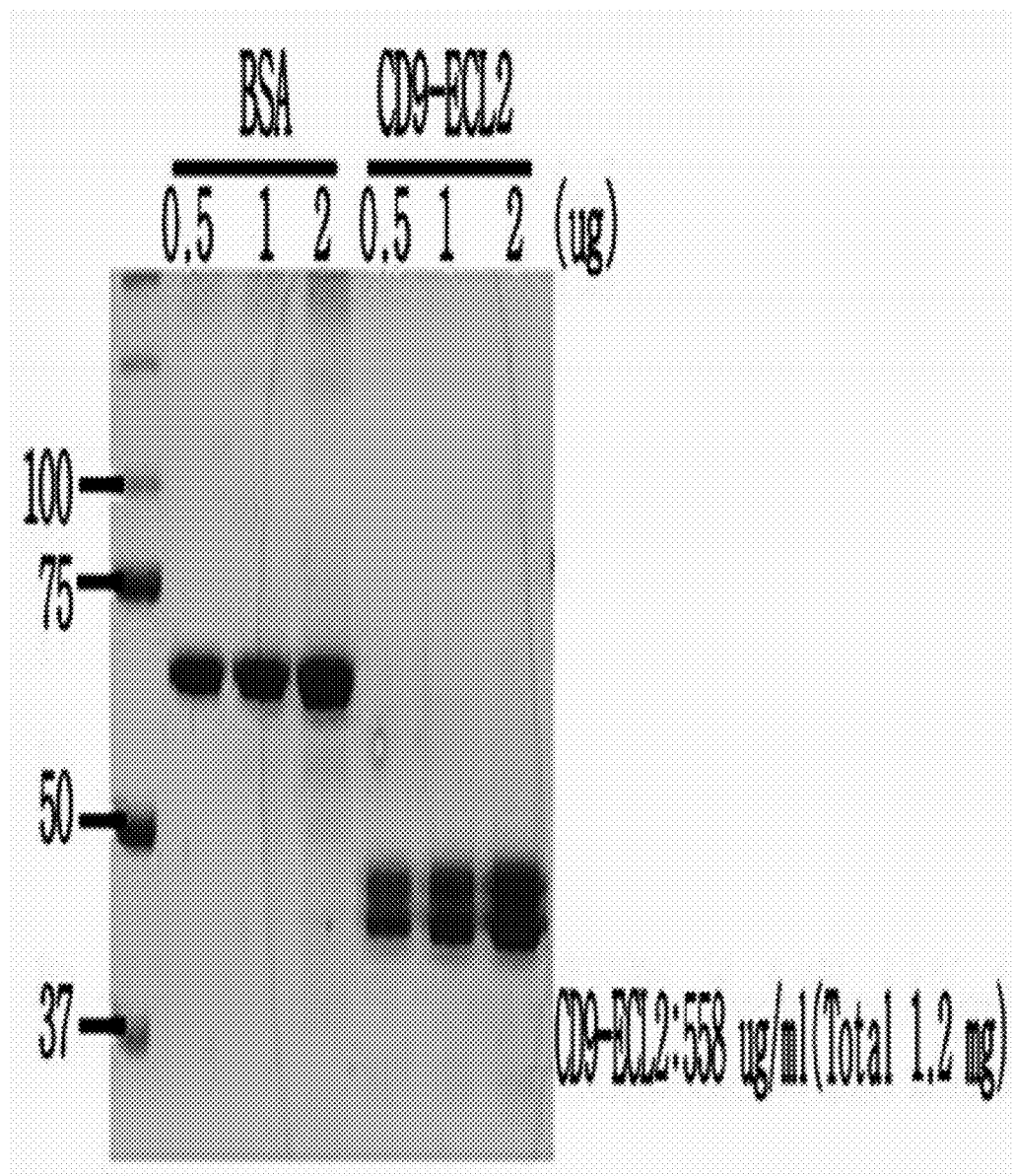
[Fig. 4]

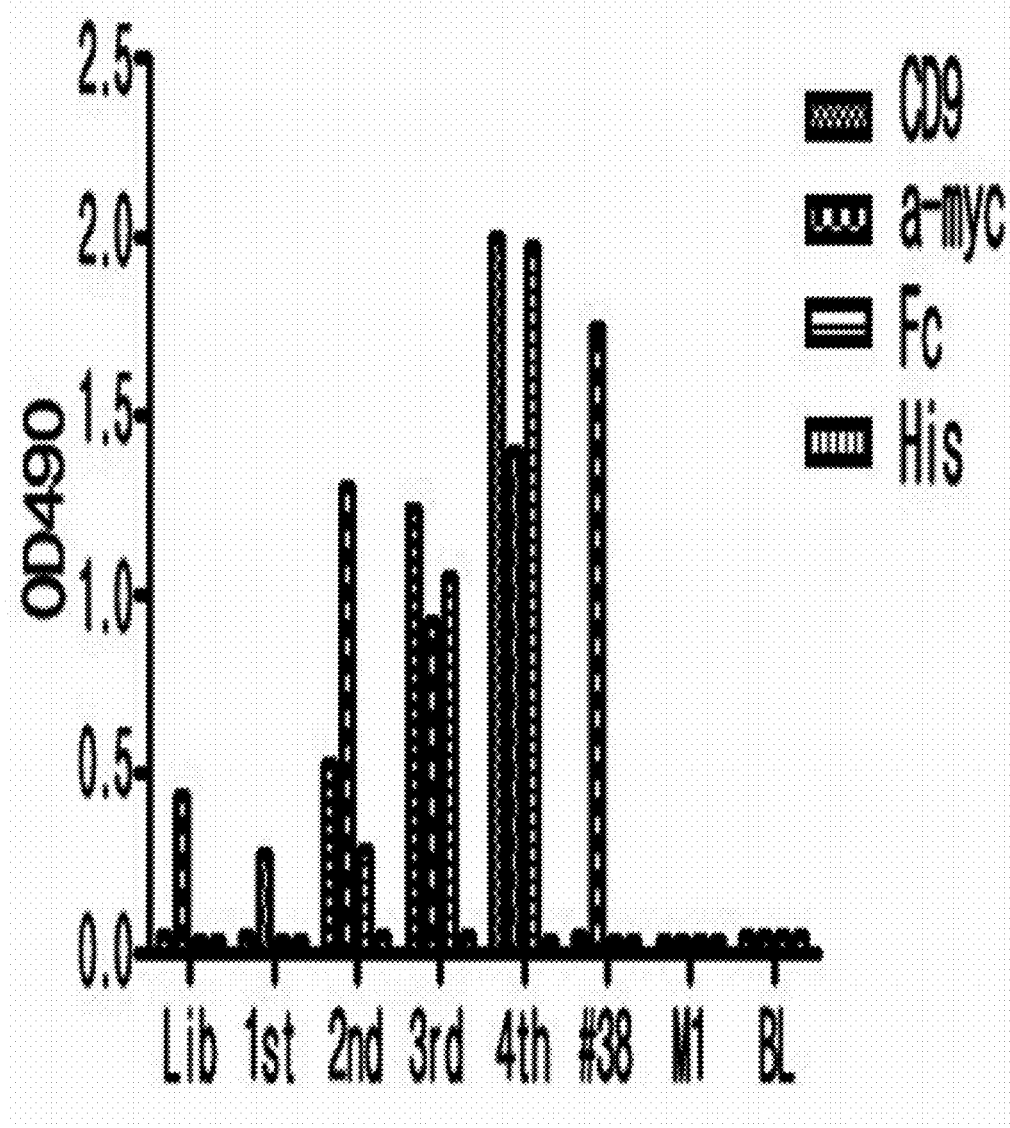
[Fig. 5]

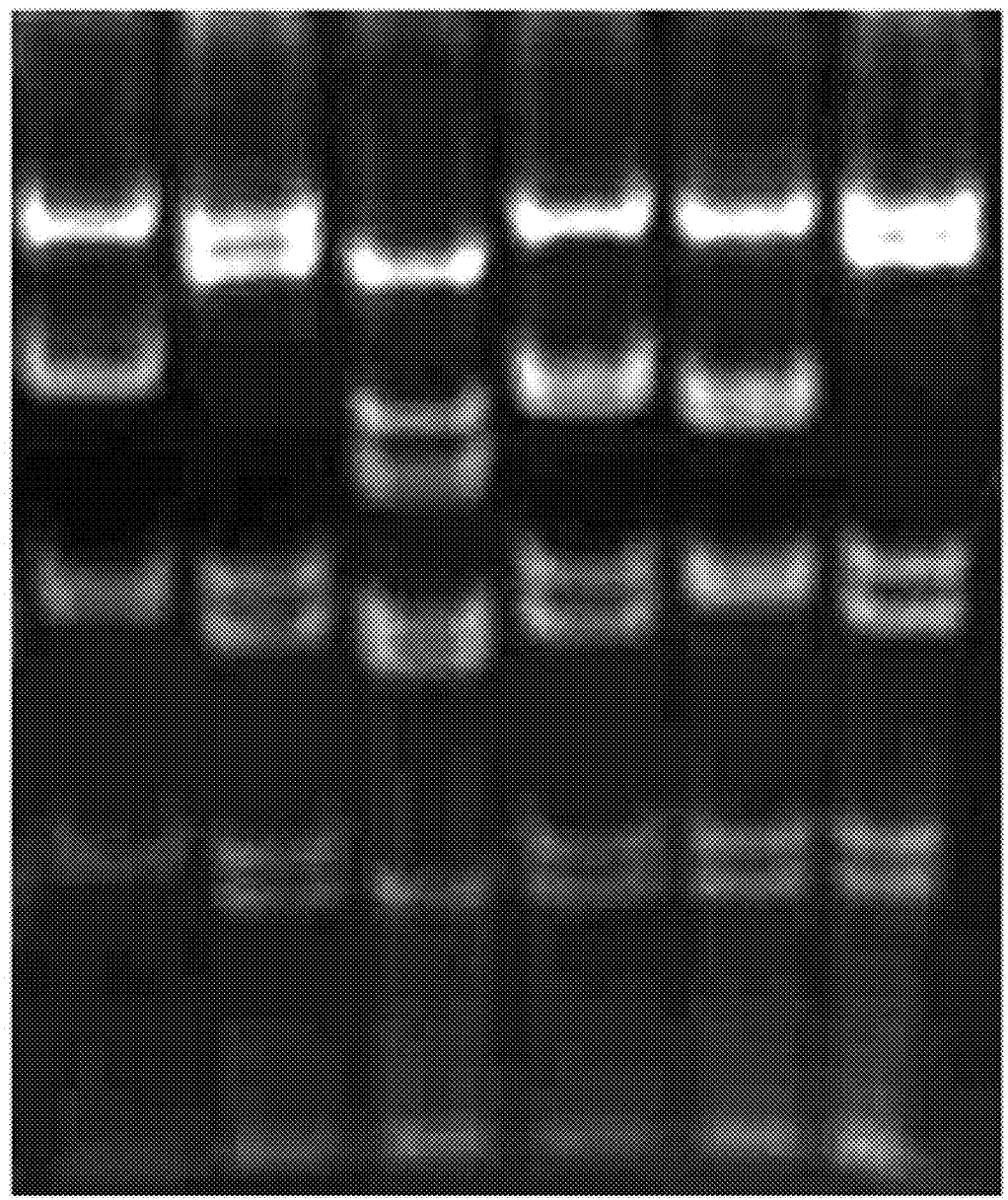
[Fig. 6]

[Fig. 7]
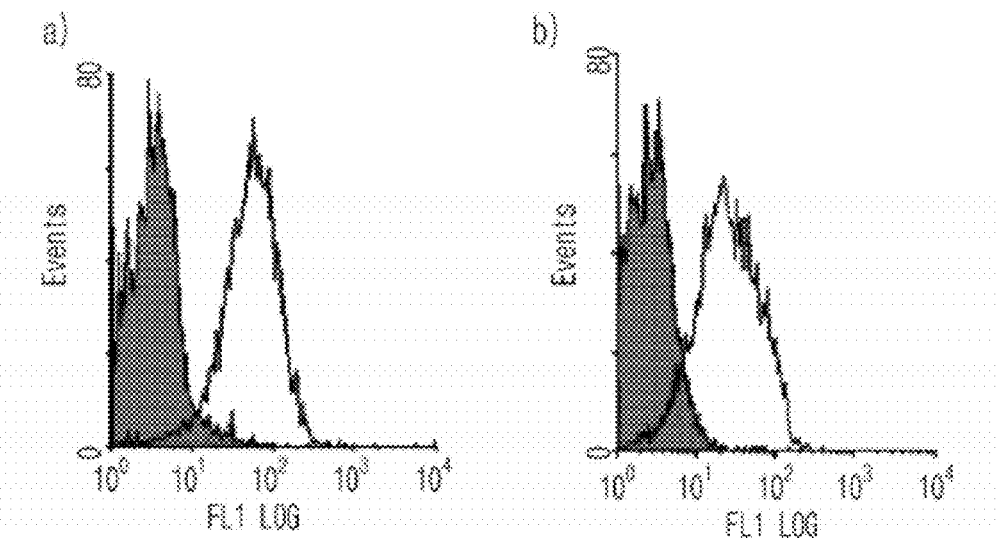
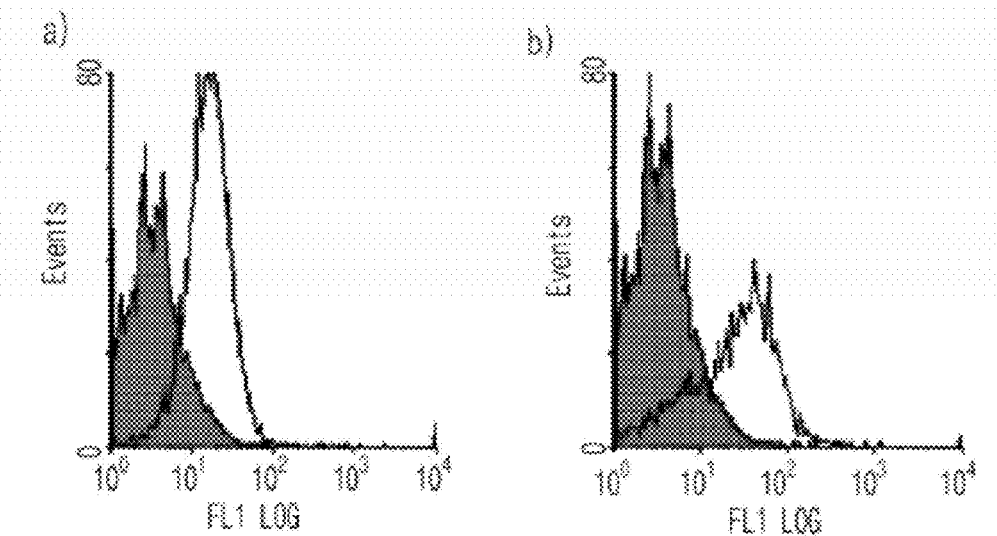

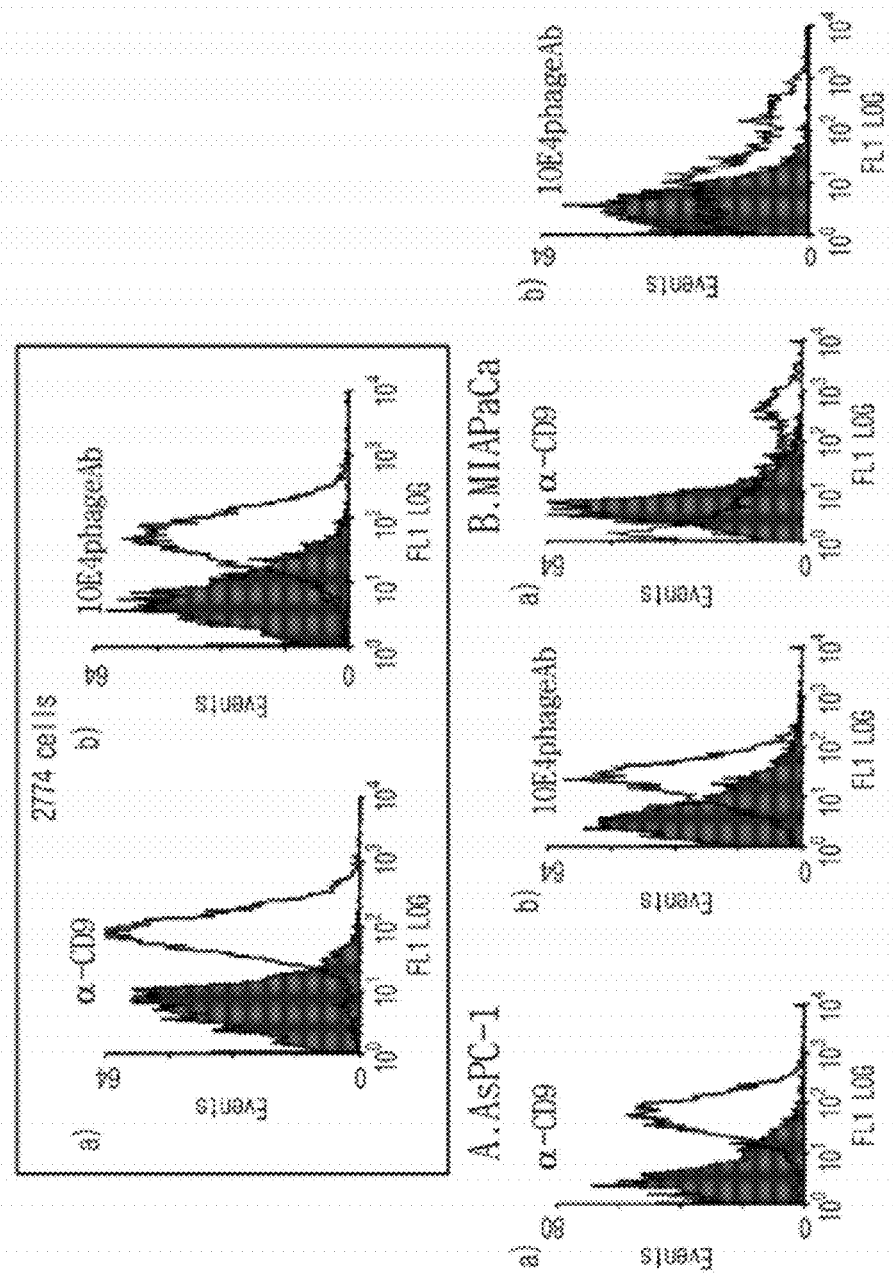

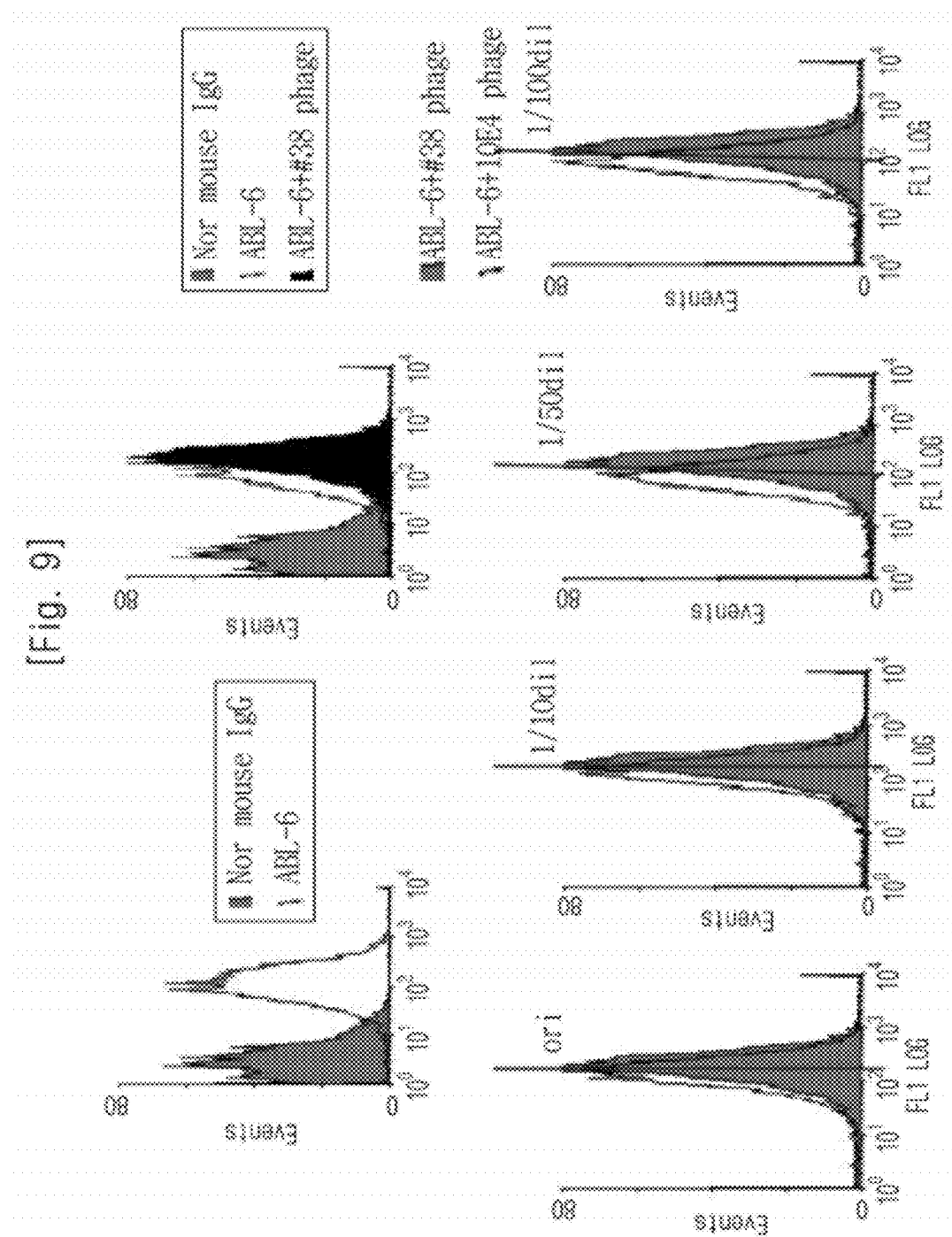
[Fig. 9]

[Fig. 10]
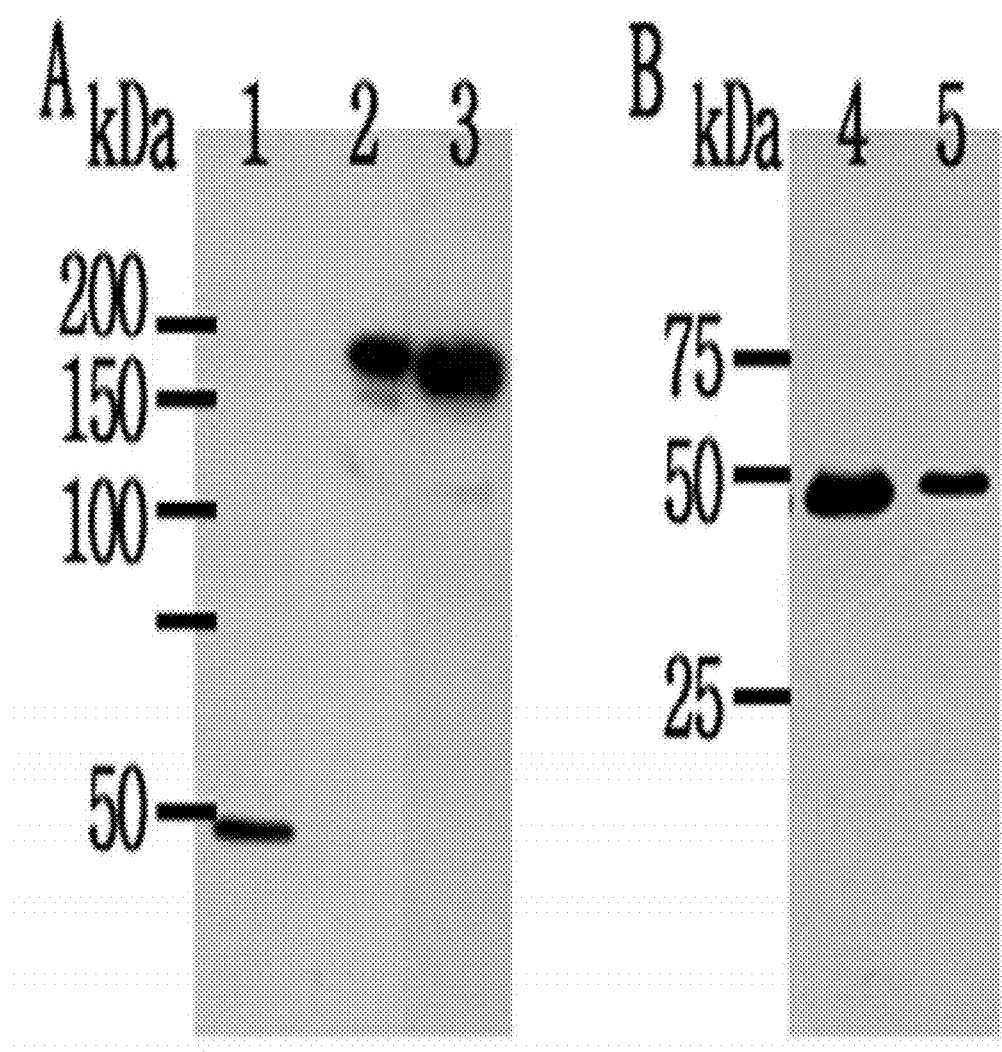

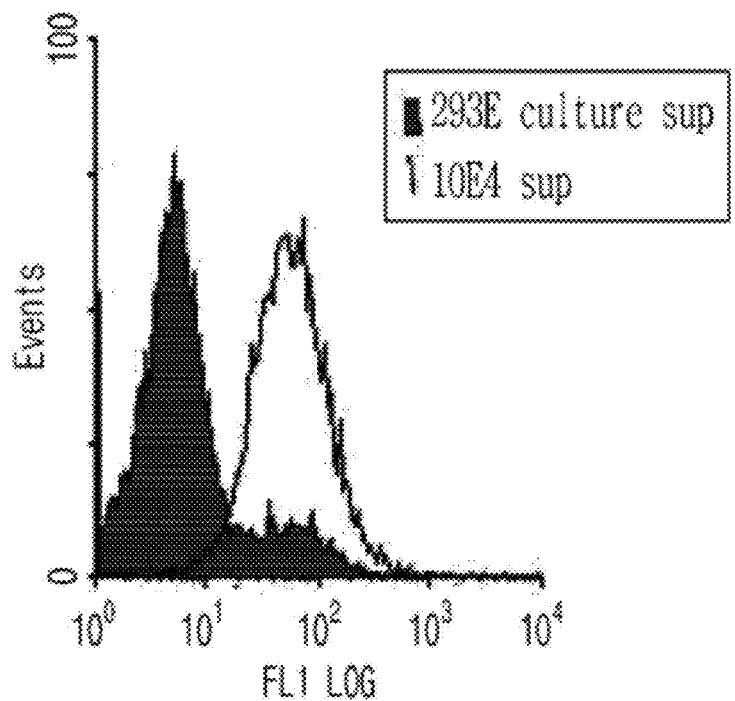

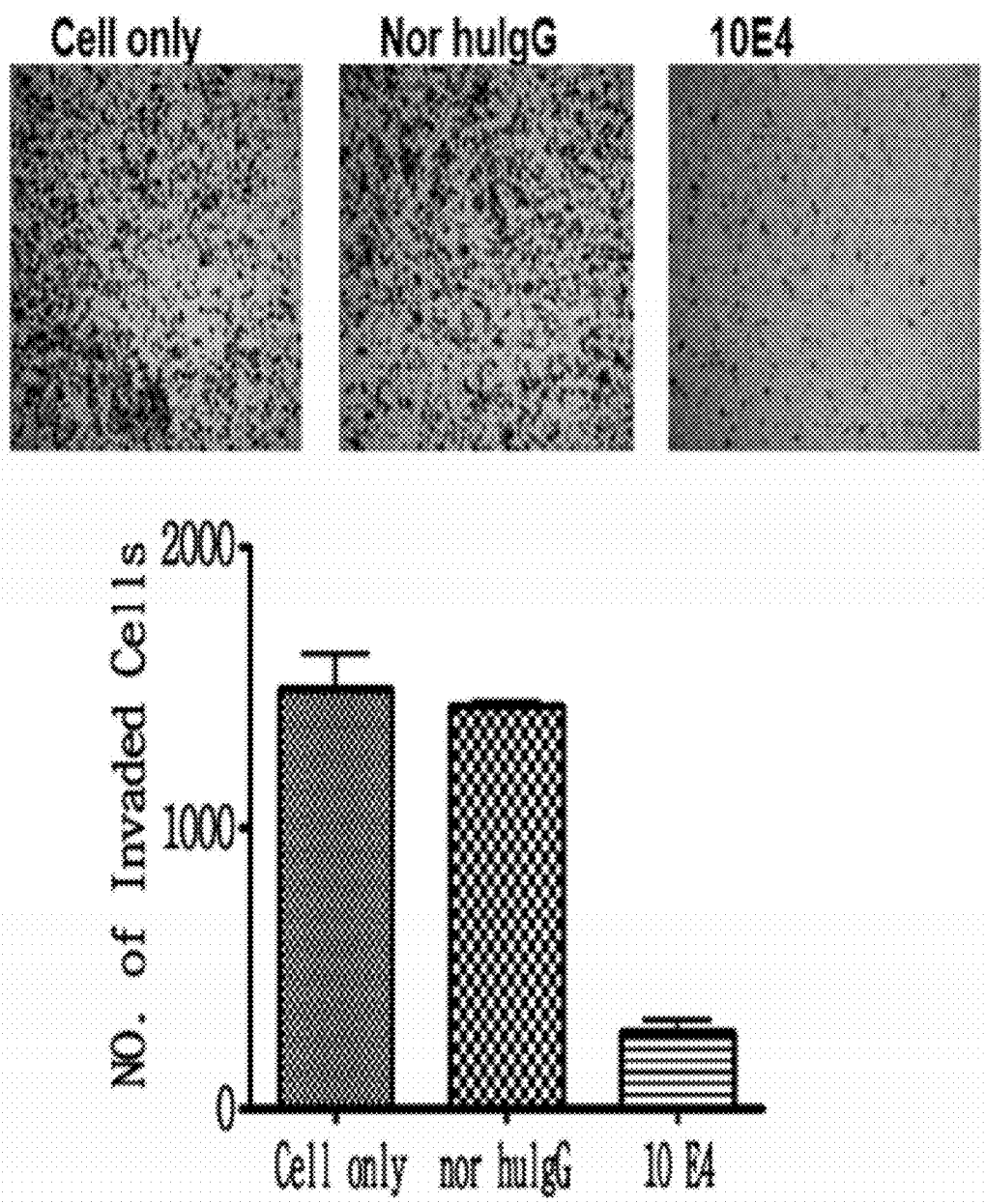
[Fig. 12]

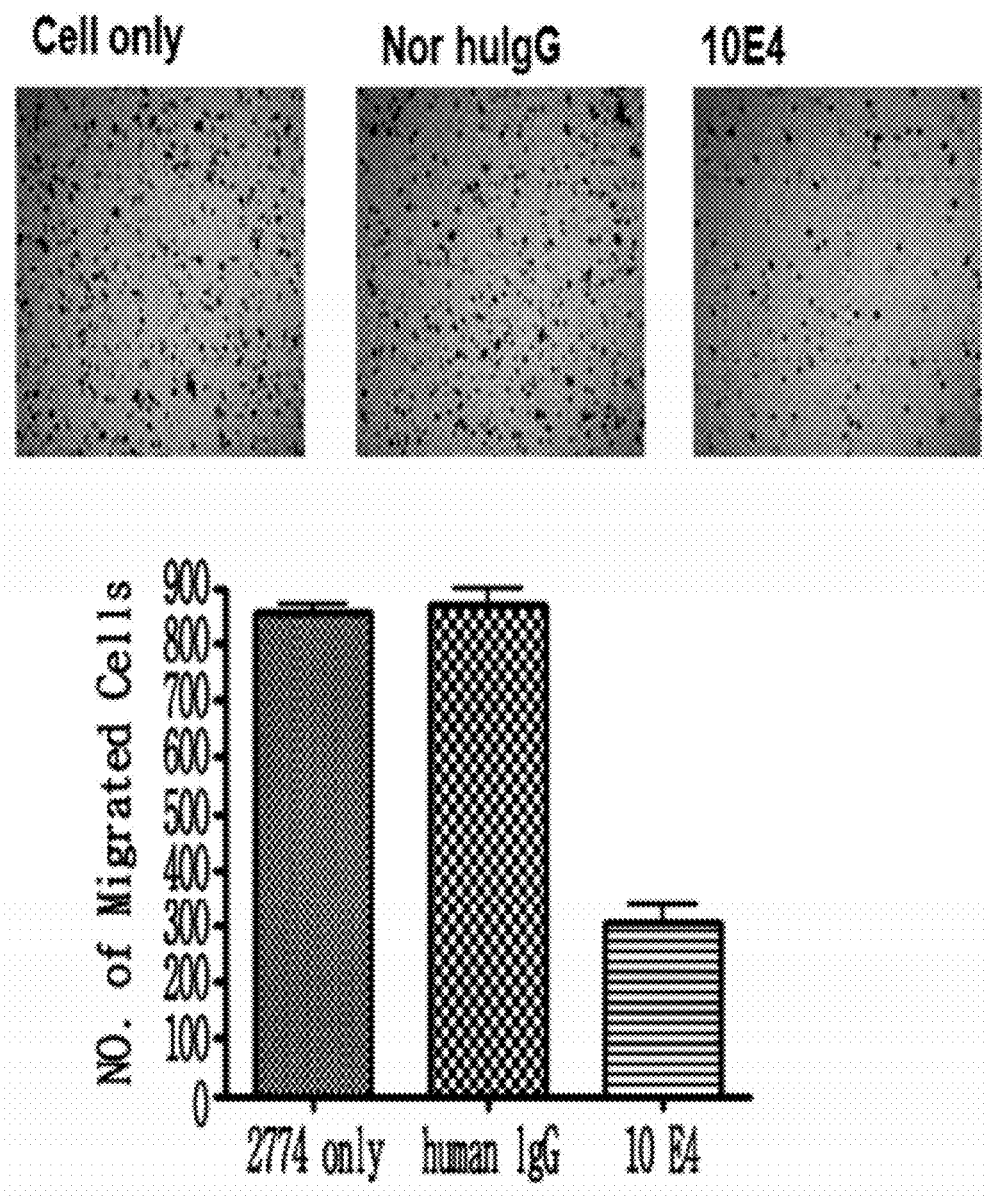
[Fig. 13]

[Fig. 14]
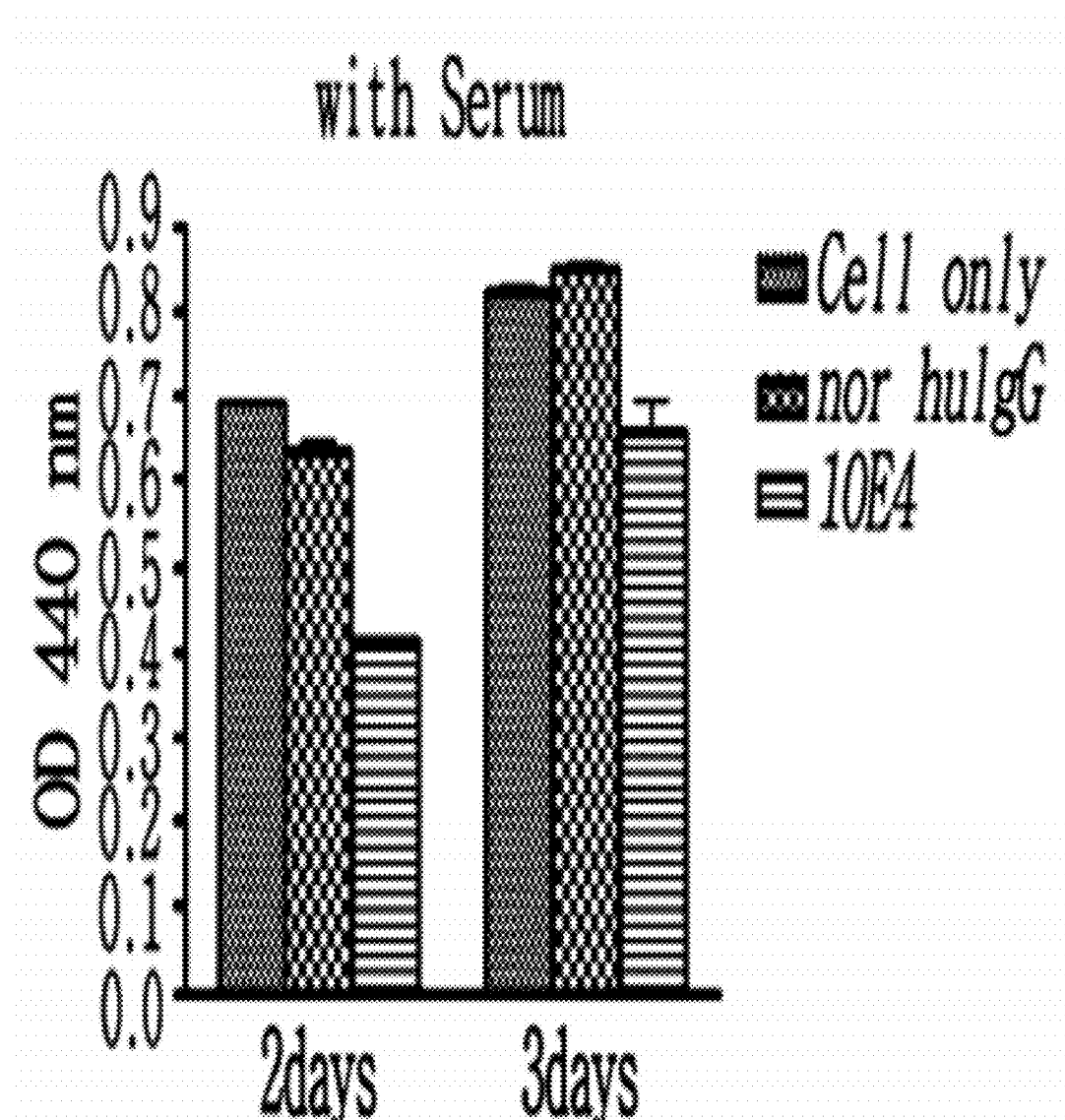

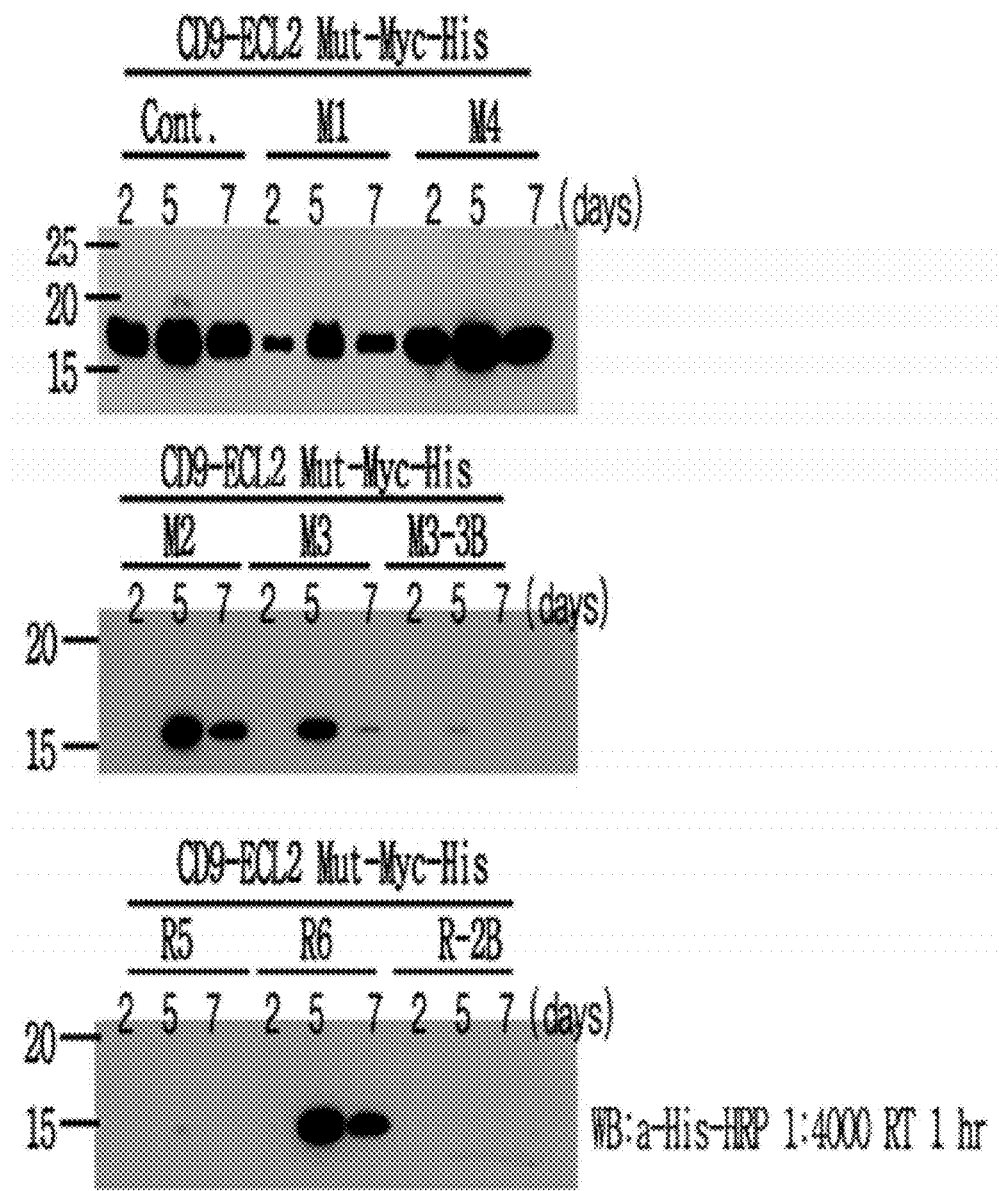
[Fig. 15]

SEQUENCE LISTING

```
<160> NUMBER OF SEQ ID NOS: 76

<210> SEQ ID NO 1
<211> LENGTH: 38
<212> TYPE: DNA
<213> ORGANISM: Artificial Sequence
<220> FEATURE:
<223> OTHER INFORMATION: CD9-ECL2 forward primer

<400> SEQUENCE: 1 caggggccg tggggcctc ccacaaggat gaggtgat                                 38

<210> SEQ ID NO 2
<211> LENGTH: 39
<212> TYPE: DNA
<213> ORGANISM: Artificial Sequence
<220> FEATURE:
<223> OTHER INFORMATION: CD9-ECL2 reverse primer

<400> SEQUENCE: 2
tagcggccga cgcggccaag atgtggaatt tattgtcga                              39

<210> SEQ ID NO 3
<211> LENGTH: 380
<212> TYPE: PRT
<213> ORGANISM: Artificial Sequence
<220> FEATURE:
<223> OTHER INFORMATION: Synthetic peptide
<220> FEATURE:
<221> NAME/KEY: SITE
<222> LOCATION: (1)..(20)
<223> OTHER INFORMATION: Reader sequence
<220> FEATURE:
<221> NAME/KEY: SITE
<222> LOCATION: (21)..(25)
<223> OTHER INFORMATION: Sfi I
<220> FEATURE:
<221> NAME/KEY: SITE
<222> LOCATION: (110)..(114)
<223> OTHER INFORMATION: Sfi I
<220> FEATURE:
<221> NAME/KEY: SITE
<222> LOCATION: (117)..(122)
<223> OTHER INFORMATION: 6X His
<220> FEATURE:
<221> NAME/KEY: SITE
<222> LOCATION: (125)..(130)
<223> OTHER INFORMATION: Trombin site
<220> FEATURE:
<221> NAME/KEY: SITE
<222> LOCATION: (131)..(357)
```

```
<223> OTHER INFORMATION: Fc
<220> FEATURE:
<221> NAME/KEY: SITE
<222> LOCATION: (358)..(367)
<223> OTHER INFORMATION: Myc
<220> FEATURE:
<221> NAME/KEY: SITE
<222> LOCATION: (373)..(380)
<223> OTHER INFORMATION: 8X His

<400> SEQUENCE: 3

Met Gly Trp Ser Tyr Ile Ile Leu Phe Leu Val Ala Thr Ala Thr Asp
1               5                   10                  15

Val His Ser Gln Gly Ala Val Gly Ala Ser His Lys Asp Glu Val Ile
            20                  25                  30

Lys Glu Val Gln Glu Phe Tyr Lys Asp Thr Tyr Asn Lys Leu Lys Thr
        35                  40                  45

Lys Asp Glu Pro Gln Arg Glu Thr Leu Lys Ala Ile His Tyr Ala Leu
    50                  55                  60

Asn Cys Cys Gly Leu Ala Gly Gly Val Glu Gln Phe Ile Ser Asp Ile
65                  70                  75                  80

Cys Pro Lys Lys Asp Val Leu Glu Thr Phe Thr Val Lys Ser Cys Pro
                85                  90                  95

Asp Ala Ile Lys Glu Val Phe Asp Asn Lys Phe His Ile Leu Ala Ala
            100                 105                 110

Ser Ala Ala Ser His His His His His His Ser Gly Leu Val Pro Arg
        115                 120                 125

Gly Ser Asp Lys Thr His Thr Cys Pro Pro Cys Pro Ala Pro Glu Leu
    130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys Glu Gln Lys Leu Ile Ser Glu Glu Asp Leu Asn
        355                 360                 365
```

Ser Ala Val Asp His His His His His His His
        370                 375                 380

<210> SEQ ID NO 4
<211> LENGTH: 23
<212> TYPE: DNA
<213> ORGANISM: Artificial Sequence
<220> FEATURE:
<223> OTHER INFORMATION: Forward primer-pelB5

<400> SEQUENCE: 4
ctagataacg agggcaaatc atg                                        23

<210> SEQ ID NO 5
<211> LENGTH: 19
<212> TYPE: DNA
<213> ORGANISM: Artificial Sequence
<220> FEATURE:
<223> OTHER INFORMATION: Reverse primer-cla3

<400> SEQUENCE: 5
cgtcaccaat gaaaccatc                                             19

<210> SEQ ID NO 6
<211> LENGTH: 121
<212> TYPE: PRT
<213> ORGANISM: Artificial Sequence
<220> FEATURE:
<223> OTHER INFORMATION: 10E4 Heavy chain
<220> FEATURE:
<221> NAME/KEY: SITE
<222> LOCATION: (1)..(32)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(110)
<223> OTHER INFORMATION: CDR3
<220> FEATURE:
<221> NAME/KEY: SITE
<222> LOCATION: (111)..(121)
<223> OTHER INFORMATION: FR4

<400> SEQUENCE: 6

Met Ala Gln Val Gln Leu Val Gln Ser Gly Gly Gly Leu Val Gln Pro
1               5                   10                  15

Gly Arg Ser Leu Arg Leu Ser Cys Ala Ala Ser Gly Phe Thr Phe Asp
            20                  25                  30

Asp Phe Ala Met His Trp Val Arg Gln Ala Pro Gly Lys Gly Leu Glu
        35                  40                  45

Trp Val Ala Gly Ile Ser Trp Asn Ser Gly Asp Ile Arg Tyr Ala Asp
    50                  55                  60

Ser Val Arg Gly Arg Phe Thr Ile Ser Arg Asp Asn Ala Lys Asn Ser
65                  70                  75                  80

```
Leu Phe Leu Gln Met Asn Ser Leu Arg Ala Glu Asp Thr Ala Val Tyr
                85                  90                  95

Tyr Cys Ala Arg Ser Pro Val Gly Thr Thr Tyr Phe Asp Tyr Trp Gly
            100                 105                 110

Gln Gly Ala Leu Ile Thr Val Ser Ser
        115                 120

<210> SEQ ID NO 7
<211> LENGTH: 5
<212> TYPE: PRT
<213> ORGANISM: Artificial Sequence
<220> FEATURE:
<223> OTHER INFORMATION: Synthetic peptide

<400> SEQUENCE: 7

Asp Phe Ala Met His
1               5

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Gly Ile Ser Trp Asn Ser Gly Asp Ile Arg Tyr Ala Asp Ser Val Arg
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Ser Pro Val Gly Thr Thr Tyr Phe Asp Tyr
1               5                   10

<210> SEQ ID NO 10
<211> LENGTH: 107
<212> TYPE: PRT
<213> ORGANISM: Artificial Sequence
<220> FEATURE:
<223> OTHER INFORMATION: 10E4 Light chain
<220> FEATURE:
<221> NAME/KEY: SITE
<222> LOCATION: (1)..(23)
<223> OTHER INFORMATION: FR1
<220> FEATURE:
<221> NAME/KEY: SITE
<222> LOCATION: (24)..(34)
<223> OTHER INFORMATION: CDR1
<220> FEATURE:
<221> NAME/KEY: SITE
<222> LOCATION: (35)..(49)
<223> OTHER INFORMATION: FR2
<220> FEATURE:
<221> NAME/KEY: SITE
<222> LOCATION: (50)..(56)
<223> OTHER INFORMATION: CDR2
<220> FEATURE:
<221> NAME/KEY: SITE
<222> LOCATION: (57)..(88)
<223> OTHER INFORMATION: FR3
<220> FEATURE:
<221> NAME/KEY: SITE
```

```
<222> LOCATION: (89)..(97)
<223> OTHER INFORMATION: CDR3
<220> FEATURE:
<221> NAME/KEY: SITE
<222> LOCATION: (98)..(107)
<223> OTHER INFORMATION: FR4

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Glu Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ile Phe Pro Leu
                85                  90                  95

Thr Phe Gly Gly Thr Lys Val Asp Ile Lys Arg
            100                 105

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

Arg Ala Ser Gln Gly Ile Ser Ser Tyr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthetic peptide

<400> SEQUENCE: 12

Ala Ala Ser Thr Leu Gln Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic peptide

<400> SEQUENCE: 13

Gln Gln Leu Asn Ile Phe Pro Leu Thr
1               5

<210> SEQ ID NO 14
<211> LENGTH: 50
<212> TYPE: DNA
<213> ORGANISM: Artificial Sequence
<220> FEATURE:
<223> OTHER INFORMATION: Forward primer-NATVH1-1

<400> SEQUENCE: 14
ttggtggcca cagcggccga tgtccactcg caggtgcagc tggtgcagtc            50
```

<210> SEQ ID NO 15
<211> LENGTH: 26
<212> TYPE: DNA
<213> ORGANISM: Artificial Sequence
<220> FEATURE:
<223> OTHER INFORMATION: Reverse primer-NATJH-ALL

<400> SEQUENCE: 15
gaggaggcta gctgaggaga cggtga                                         26

<210> SEQ ID NO 16
<211> LENGTH: 53
<212> TYPE: DNA
<213> ORGANISM: Artificial Sequence
<220> FEATURE:
<223> OTHER INFORMATION: Forward primer-NATVK6

<400> SEQUENCE: 16
ttggtggcca cagcggccga tgtccactcg gacatccaga tgacccagtc tcc           53

<210> SEQ ID NO 17
<211> LENGTH: 30
<212> TYPE: DNA
<213> ORGANISM: Artificial Sequence
<220> FEATURE:
<223> OTHER INFORMATION: Reverse primer-NATJK-CD910E4

<400> SEQUENCE: 17
gaggagagat cttttgatat ccactttggt                                     30

<210> SEQ ID NO 18
<211> LENGTH: 38
<212> TYPE: DNA
<213> ORGANISM: Artificial Sequence
<220> FEATURE:
<223> OTHER INFORMATION: Forward primer F602 F

<400> SEQUENCE: 18 caggggggccg tgggggcctc ccacaaggat gaggtgat                           38

<210> SEQ ID NO 19
<211> LENGTH: 54
<212> TYPE: DNA
<213> ORGANISM: Artificial Sequence
<220> FEATURE:
<223> OTHER INFORMATION: Forward primer F602 M1

<400> SEQUENCE: 19
tcccacaagg atgaggtgat taaggaactc caggagtttt acaaggacac ctac          54

<210> SEQ ID NO 20
<211> LENGTH: 43
<212> TYPE: DNA
<213> ORGANISM: Artificial Sequence
<220> FEATURE:
<223> OTHER INFORMATION: Forward primer F602 M2

<400> SEQUENCE: 20
ttttacaagg acacctacca aaagctgaga aacaaggatg agc                      43

<210> SEQ ID NO 21
<211> LENGTH: 60
<212> TYPE: DNA
<213> ORGANISM: Artificial Sequence
<220> FEATURE:
<223> OTHER INFORMATION: Reverse primer F602 M3

-continued

```
<400> SEQUENCE: 21
ctgagataaa ctgttccacg cccccagcga taccacagca gttcaacgcc atgtggatgg      60

<210> SEQ ID NO 22
<211> LENGTH: 65
<212> TYPE: DNA
<213> ORGANISM: Artificial Sequence
<220> FEATURE:
<223> OTHER INFORMATION: Reverse primer F602 M4

<400> SEQUENCE: 22
ggacttcact tggaaggatt cgagtacttg cttcttgggg cagatgtctg agataaactg      60
ttcca                                                                  65

<210> SEQ ID NO 23
<211> LENGTH: 62
<212> TYPE: DNA
<213> ORGANISM: Artificial Sequence
<220> FEATURE:
<223> OTHER INFORMATION: Reverse primer F602 M5

<400> SEQUENCE: 23
gatgtggaat ttacgtggaa gacctcatcg atggcatcag acaggactt cacttggaag       60 ga                                                                     62

<210> SEQ ID NO 24
<211> LENGTH: 56
<212> TYPE: DNA
<213> ORGANISM: Artificial Sequence
<220> FEATURE:
<223> OTHER INFORMATION: Reverse primer F602 M6

<400> SEQUENCE: 24
tagcggccga cgcggccaag atgtggaatt tactgtggaa gacctcatcg atggca          56

<210> SEQ ID NO 25
<211> LENGTH: 39
<212> TYPE: DNA
<213> ORGANISM: Artificial Sequence
<220> FEATURE:
<223> OTHER INFORMATION: Reverse primer F602 R

<400> SEQUENCE: 25
tagcggccga cgcggccaag atgtggaatt tattgtcga                             39

<210> SEQ ID NO 26
<211> LENGTH: 137
<212> TYPE: PRT
<213> ORGANISM: Artificial Sequence
<220> FEATURE:
<223> OTHER INFORMATION: pYK602-Myc-His CD009 wild type

<400> SEQUENCE: 26

Met Gly Trp Ser Tyr Ile Ile Leu Phe Leu Val Ala Thr Ala Thr Asp
1               5                   10                  15

Val His Ser Gln Gly Ala Val Gly Ala Ser His Lys Asp Glu Val Ile
                20                  25                  30

Lys Glu Val Gln Glu Phe Tyr Lys Asp Thr Tyr Asn Lys Leu Lys Thr
            35                  40                  45

Lys Asp Glu Pro Gln Arg Glu Thr Leu Lys Ala Ile His Tyr Ala Leu
        50                  55                  60

Asn Cys Cys Gly Leu Ala Gly Gly Val Glu Gln Phe Ile Ser Asp Ile
```

```
                65                  70                  75                  80
Cys Pro Lys Lys Asp Val Leu Glu Thr Phe Thr Val Lys Ser Cys Pro
                85                  90                  95

Asp Ala Ile Lys Glu Val Phe Asp Asn Lys Phe His Ile Leu Ala Ala
            100                 105                 110

Ser Ala Glu Gln Lys Leu Ile Ser Glu Glu Asp Leu Asn Ser Ala Val
        115                 120                 125

Asp His His His His His His His
        130                 135

<210> SEQ ID NO 27
<211> LENGTH: 84
<212> TYPE: PRT
<213> ORGANISM: Artificial Sequence
<220> FEATURE:
<223> OTHER INFORMATION: Synthetic peptide

<400> SEQUENCE: 27

Ser His Lys Asp Glu Val Ile Lys Glu Val Gln Glu Phe Tyr Lys Asp
1               5                   10                  15

Thr Tyr Asn Lys Leu Lys Thr Lys Asp Glu Pro Gln Arg Glu Thr Leu
            20                  25                  30

Lys Ala Ile His Tyr Ala Leu Asn Cys Cys Gly Leu Ala Gly Gly Val
        35                  40                  45

Glu Gln Phe Ile Ser Asp Ile Cys Pro Lys Lys Asp Val Leu Glu Thr
    50                  55                  60

Phe Thr Val Lys Ser Cys Pro Asp Ala Ile Lys Glu Val Phe Asp Asn
65                  70                  75                  80

Lys Phe His Ile

<210> SEQ ID NO 28
<211> LENGTH: 84
<212> TYPE: PRT
<213> ORGANISM: Artificial Sequence
<220> FEATURE:
<223> OTHER INFORMATION: Synthetic peptide

<400> SEQUENCE: 28

Ser His Lys Asp Glu Val Ile Lys Glu Val Gln Glu Phe Tyr Lys Asp
1               5                   10                  15

Thr Tyr Asn Lys Leu Lys Thr Lys Asp Glu Pro Gln Arg Glu Thr Leu
            20                  25                  30

Lys Ala Ile His Tyr Ala Leu Asn Cys Cys Gly Leu Ala Gly Gly Val
        35                  40                  45

Glu Gln Phe Ile Ser Asp Ile Cys Pro Lys Lys Asp Val Leu Glu Thr
    50                  55                  60

Phe Thr Val Lys Ser Cys Pro Asp Ala Ile Asp Glu Val Phe His Ser
65                  70                  75                  80

Lys Phe His Ile

<210> SEQ ID NO 29
<211> LENGTH: 84
<212> TYPE: PRT
<213> ORGANISM: Artificial Sequence
<220> FEATURE:
<223> OTHER INFORMATION: Synthetic peptide

<400> SEQUENCE: 29

Ser His Lys Asp Glu Val Ile Lys Glu Val Gln Glu Phe Tyr Lys Asp
1               5                   10                  15
```

Thr Tyr Asn Lys Leu Lys Thr Lys Asp Glu Pro Gln Arg Glu Thr Leu
            20                  25                  30

Lys Ala Ile His Tyr Ala Leu Asn Cys Cys Gly Leu Ala Gly Gly Val
        35                  40                  45

Glu Gln Phe Ile Ser Asp Ile Cys Pro Lys Lys Val Leu Glu Ser
    50                  55                  60

Phe Gln Val Lys Ser Cys Pro Asp Ala Ile Asp Glu Val Phe His Ser
65                  70                  75                  80

Lys Phe His Ile

<210> SEQ ID NO 30
<211> LENGTH: 84
<212> TYPE: PRT
<213> ORGANISM: Artificial Sequence
<220> FEATURE:
<223> OTHER INFORMATION: Synthetic peptide

<400> SEQUENCE: 30

Ser His Lys Asp Glu Val Ile Lys Glu Val Gln Glu Phe Tyr Lys Asp
1               5                   10                  15

Thr Tyr Asn Lys Leu Lys Thr Lys Asp Glu Pro Gln Arg Glu Thr Leu
            20                  25                  30

Lys Ala Ile His Met Ala Leu Asn Cys Cys Gly Ile Ala Gly Gly Val
        35                  40                  45

Glu Gln Phe Ile Ser Asp Ile Cys Pro Lys Lys Gln Val Leu Glu Ser
    50                  55                  60

Phe Gln Val Lys Ser Cys Pro Asp Ala Ile Asp Glu Val Phe His Ser
65                  70                  75                  80

Lys Phe His Ile

<210> SEQ ID NO 31
<211> LENGTH: 84
<212> TYPE: PRT
<213> ORGANISM: Artificial Sequence
<220> FEATURE:
<223> OTHER INFORMATION: Synthetic peptide

<400> SEQUENCE: 31

Ser His Lys Asp Glu Val Ile Lys Glu Val Gln Glu Phe Tyr Lys Asp
1               5                   10                  15

Thr Tyr Asn Lys Leu Lys Thr Lys Asp Glu Pro Gln Arg Glu Thr Leu
            20                  25                  30

Lys Ala Ile His Met Ala Leu Asn Cys Cys Gly Ile Ala Gly Gly Val
        35                  40                  45

Val Gln Phe Ile Ser Asp Ile Cys Pro Lys Lys Gln Val Leu Glu Ser
    50                  55                  60

Phe Gln Val Lys Ser Cys Pro Asp Ala Ile Asp Glu Val Phe His Ser
65                  70                  75                  80

Lys Phe His Ile

<210> SEQ ID NO 32
<211> LENGTH: 84
<212> TYPE: PRT
<213> ORGANISM: Artificial Sequence
<220> FEATURE:
<223> OTHER INFORMATION: Synthetic peptide

<400> SEQUENCE: 32

Ser His Lys Asp Glu Val Ile Lys Glu Leu Gln Glu Phe Tyr Lys Asp

```
                1               5                  10                 15
Thr Tyr Gln Lys Leu Arg Asn Lys Asp Glu Pro Gln Arg Glu Thr Leu
            20                  25                 30

Lys Ala Ile His Tyr Ala Leu Asn Cys Cys Gly Leu Ala Gly Gly Val
            35                  40                 45

Glu Gln Phe Ile Ser Asp Ile Cys Pro Lys Lys Asp Val Leu Glu Thr
    50                  55                  60

Phe Thr Val Lys Ser Cys Pro Asp Ala Ile Lys Glu Val Phe Asp Asn
65                  70                  75                  80

Lys Phe His Ile

<210> SEQ ID NO 33
<211> LENGTH: 84
<212> TYPE: PRT
<213> ORGANISM: Artificial Sequence
<220> FEATURE:
<223> OTHER INFORMATION: Synthetic peptide

<400> SEQUENCE: 33

Ser His Lys Asp Glu Val Ile Lys Glu Leu Gln Ala Phe Tyr Lys Asp
1               5                   10                  15

Thr Tyr Gln Lys Leu Arg Asn Lys Asp Glu Pro Gln Arg Glu Thr Leu
            20                  25                  30

Lys Ala Ile Leu Met Ala Leu Asn Cys Cys Gly Ile Ala Gly Gly Val
            35                  40                  45

Glu Gln Phe Ile Ser Asp Ile Cys Pro Lys Lys Gln Val Leu Glu Ser
    50                  55                  60

Phe Gln Val Lys Ser Cys Pro Asp Ala Ile Asp Glu Val Phe Pro Ser
65                  70                  75                  80

Lys Phe His Ile

<210> SEQ ID NO 34
<211> LENGTH: 84
<212> TYPE: PRT
<213> ORGANISM: Artificial Sequence
<220> FEATURE:
<223> OTHER INFORMATION: Synthetic peptide

<400> SEQUENCE: 34

Ser His Lys Asp Glu Val Ile Lys Glu Leu Gln Glu Phe Tyr Lys Asp
1               5                   10                  15

Thr Tyr Gln Lys Leu Arg Asn Lys Asp Glu Pro Gln Arg Glu Thr Leu
            20                  25                  30

Lys Ala Ile His Met Ala Leu Asn Cys Cys Gly Ile Ala Gly Gly Val
            35                  40                  45

Glu Gln Phe Ile Ser Asp Ile Cys Pro Lys Lys Gln Val Leu Glu Ser
    50                  55                  60

Phe Gln Val Lys Ser Cys Pro Asp Ala Ile Asp Glu Val Phe His Ser
65                  70                  75                  80

Lys Phe His Ile

<210> SEQ ID NO 35
<211> LENGTH: 84
<212> TYPE: PRT
<213> ORGANISM: Artificial Sequence
<220> FEATURE:
<223> OTHER INFORMATION: Synthetic peptide

<400> SEQUENCE: 35
```

-continued

```
Ser His Lys Asp Glu Val Ile Lys Glu Val Gln Phe Tyr Lys Asp
1               5                   10                  15

Thr Tyr Gln Lys Arg Arg Asn Lys Asp Glu Pro Gln Arg Glu Thr Leu
                20                  25                  30

Lys Ala Ile His Met Ala Leu Asn Cys Cys Gly Ile Ala Gly Gly Val
            35                  40                  45

Glu Gln Phe Ile Ser Asp Ile Cys Pro Lys Lys Gln Val Leu Glu Ser
        50                  55                  60

Phe Gln Val Lys Ser Cys Pro Asp Ala Ile Asp Glu Val Phe His Ser
65                  70                  75                  80

Lys Phe His Ile
```

<210> SEQ ID NO 36
<211> LENGTH: 6
<212> TYPE: PRT
<213> ORGANISM: Artificial Sequence
<220> FEATURE:
<223> OTHER INFORMATION: epitope in CD9-ECL2 domain

<400> SEQUENCE: 36

```
Lys Glu Val Phe Asp Asn
1               5
```

<210> SEQ ID NO 37
<211> LENGTH: 118
<212> TYPE: PRT
<213> ORGANISM: Artificial Sequence
<220> FEATURE:
<223> OTHER INFORMATION: 11G heavy chain
<220> FEATURE:
<221> NAME/KEY: SITE
<222> LOCATION: (1)..(32)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(107)
<223> OTHER INFORMATION: CDR3
<220> FEATURE:
<221> NAME/KEY: SITE
<222> LOCATION: (108)..(118)
<223> OTHER INFORMATION: FR4

<400> SEQUENCE: 37

```
Met Ala Gln Val Gln Leu Val Gln Ser Gly Ala Glu Val Lys Lys Pro
1               5                   10                  15

Gly Ala Ser Val Lys Leu Ser Cys Lys Ala Ser Gly Tyr Thr Ser Ser
                20                  25                  30

Ser Tyr Trp Met His Trp Val Arg Gln Ala Pro Gly Gln Arg Leu Glu
            35                  40                  45

Trp Met Gly Glu Ile Asn Pro Gly Asn Gly His Thr Asn Tyr Asn Glu
        50                  55                  60
```

```
Lys Phe Lys Ser Arg Val Thr Ile Thr Val Asp Lys Ser Ala Ser Thr
 65                  70                  75                  80

Ala Tyr Met Glu Leu Ser Ser Leu Arg Ser Glu Asp Thr Ala Val Tyr
                 85                  90                  95

Tyr Cys Gly Gln Asp Asn Ser Pro Pro Arg Ile Trp Gly Gln Gly Thr
            100                 105                 110

Leu Val Thr Val Ser Ser
        115

<210> SEQ ID NO 38
<211> LENGTH: 5
<212> TYPE: PRT
<213> ORGANISM: Artificial Sequence
<220> FEATURE:
<223> OTHER INFORMATION: Synthetic peptide

<400> SEQUENCE: 38

Ser Tyr Trp Met His
1               5

<210> SEQ ID NO 39
<211> LENGTH: 17
<212> TYPE: PRT
<213> ORGANISM: Artificial Sequence
<220> FEATURE:
<223> OTHER INFORMATION: Synthetic peptide

<400> SEQUENCE: 39

Glu Ile Asn Pro Gly Asn Gly His Thr Asn Tyr Asn Glu Lys Phe Lys
1               5                   10                  15

Ser

<210> SEQ ID NO 40
<211> LENGTH: 7
<212> TYPE: PRT
<213> ORGANISM: Artificial Sequence
<220> FEATURE:
<223> OTHER INFORMATION: Synthetic peptide

<400> SEQUENCE: 40

Asp Asn Ser Pro Pro Arg Ile
1               5

<210> SEQ ID NO 41
<211> LENGTH: 106
<212> TYPE: PRT
<213> ORGANISM: Artificial Sequence
<220> FEATURE:
<223> OTHER INFORMATION: 11G light chain
<220> FEATURE:
<221> NAME/KEY: SITE
<222> LOCATION: (1)..(23)
<223> OTHER INFORMATION: FR1
<220> FEATURE:
<221> NAME/KEY: SITE
<222> LOCATION: (24)..(33)
<223> OTHER INFORMATION: CDR1
<220> FEATURE:
<221> NAME/KEY: SITE
<222> LOCATION: (34)..(48)
<223> OTHER INFORMATION: FR2
<220> FEATURE:
<221> NAME/KEY: SITE
<222> LOCATION: (49)..(55)
<223> OTHER INFORMATION: CDR2
<220> FEATURE:
<221> NAME/KEY: SITE
<222> LOCATION: (56)..(87)
<223> OTHER INFORMATION: FR3
```

```
<220> FEATURE:
<221> NAME/KEY: SITE
<222> LOCATION: (88)..(95)
<223> OTHER INFORMATION: CDR3
<220> FEATURE:
<221> NAME/KEY: SITE
<222> LOCATION: (96)..(106)
<223> OTHER INFORMATION: FR4

<400> SEQUENCE: 41

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Thr Ile Gly Asn Leu
            20                  25                  30

Ala Trp Phe Gln Gln Lys Pro Gly Lys Ala Pro Lys Leu Leu Ile Tyr
        35                  40                  45

Lys Ala Ser Ser Leu Glu Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Tyr Ser Asp Tyr Trp Thr Phe
                85                  90                  95

Gly Gln Gly Thr Lys Val Glu Ile Lys Arg
            100                 105

<210> SEQ ID NO 42
<211> LENGTH: 10
<212> TYPE: PRT
<213> ORGANISM: Artificial Sequence
<220> FEATURE:
<223> OTHER INFORMATION: Synthetic peptide

<400> SEQUENCE: 42

Arg Ala Ser Gln Thr Ile Gly Asn Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Synthetic peptide

<400> SEQUENCE: 43

Lys Ala Ser Ser Leu Glu Ser
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic peptide

<400> SEQUENCE: 44

Gln Gln Tyr Ser Asp Tyr Trp Thr
1               5

<210> SEQ ID NO 45
<211> LENGTH: 118
<212> TYPE: PRT
<213> ORGANISM: Artificial Sequence
<220> FEATURE:
<223> OTHER INFORMATION: 3F3 heavy chain
<220> FEATURE:
<221> NAME/KEY: SITE
```

```
<222> LOCATION: (1)..(23)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(107)
<223> OTHER INFORMATION: CDR3
<220> FEATURE:
<221> NAME/KEY: SITE
<222> LOCATION: (108)..(118)
<223> OTHER INFORMATION: FR4

<400> SEQUENCE: 45

Met Ala Gln Met Gln Leu Val Gln Ser Gly Ala Glu Val Lys Lys Pro
1               5                   10                  15
Gly Ala Ser Val Lys Leu Ser Cys Lys Ala Ser Gly Tyr Thr Phe Ser
            20                  25                  30
Ser Tyr Trp Met His Trp Val Arg Gln Ala Pro Gly Gln Arg Leu Glu
        35                  40                  45
Trp Met Gly Glu Ile Asn Pro Gly Asn Gly His Thr Asn Tyr Asn Glu
    50                  55                  60
Lys Phe Lys Ser Arg Val Thr Ile Thr Val Asp Lys Ser Ala Ser Thr
65                  70                  75                  80
Ala Tyr Met Glu Leu Ser Ser Leu Arg Ser Glu Asp Thr Ala Val Tyr
                85                  90                  95
Tyr Cys Gly Gln Asp Asn Ser Pro Pro Arg Ile Trp Gly Gln Gly Thr
            100                 105                 110
Leu Ile Thr Val Ser Ser
        115

<210> SEQ ID NO 46
<211> LENGTH: 5
<212> TYPE: PRT
<213> ORGANISM: Artificial Sequence
<220> FEATURE:
<223> OTHER INFORMATION: Synthetic peptide

<400> SEQUENCE: 46

Ser Tyr Trp Met His
1               5

<210> SEQ ID NO 47
<211> LENGTH: 17
<212> TYPE: PRT
<213> ORGANISM: Artificial Sequence
<220> FEATURE:
<223> OTHER INFORMATION: Synthetic peptide

<400> SEQUENCE: 47

Glu Ile Asn Pro Gly Asn Gly His Thr Asn Tyr Asn Glu Lys Phe Lys
1               5                   10                  15
Ser
```

```
<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Asp Asn Ser Pro Pro Arg Ile
1               5

<210> SEQ ID NO 49
<211> LENGTH: 112
<212> TYPE: PRT
<213> ORGANISM: Artificial Sequence
<220> FEATURE:
<223> OTHER INFORMATION: 3F3 light chain
<220> FEATURE:
<221> NAME/KEY: SITE
<222> LOCATION: (1)..(22)
<223> OTHER INFORMATION: FR1
<220> FEATURE:
<221> NAME/KEY: SITE
<222> LOCATION: (23)..(36)
<223> OTHER INFORMATION: CDR1
<220> FEATURE:
<221> NAME/KEY: SITE
<222> LOCATION: (37)..(51)
<223> OTHER INFORMATION: FR2
<220> FEATURE:
<221> NAME/KEY: SITE
<222> LOCATION: (52)..(58)
<223> OTHER INFORMATION: CDR2
<220> FEATURE:
<221> NAME/KEY: SITE
<222> LOCATION: (59)..(90)
<223> OTHER INFORMATION: FR3
<220> FEATURE:
<221> NAME/KEY: SITE
<222> LOCATION: (91)..(101)
<223> OTHER INFORMATION: CDR3
<220> FEATURE:
<221> NAME/KEY: SITE
<222> LOCATION: (102)..(112)
<223> OTHER INFORMATION: FR4

<400> SEQUENCE: 49

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn His Val Ser Trp Tyr Gln Gln His Pro Gly Lys Ala Pro Lys Leu
        35                  40                  45

Leu Ile Tyr Asp Val Ser Asn Arg Pro Ser Gly Val Ser Gly Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asn Tyr Tyr Cys Gly Ser Tyr Thr Ser Ser
                85                  90                  95

Ser Thr Phe Glu Val Phe Gly Thr Gly Thr Lys Val Thr Val Leu Arg
            100                 105                 110

<210> SEQ ID NO 50
<211> LENGTH: 14
<212> TYPE: PRT
<213> ORGANISM: Artificial Sequence
<220> FEATURE:
<223> OTHER INFORMATION: Synthetic peptide
```

```
<400> SEQUENCE: 50

Thr Gly Thr Ser Ser Asp Val Gly Gly Tyr Asn His Val Ser
1               5                   10

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Asp Val Ser Asn Arg Pro Ser
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic peptide

<400> SEQUENCE: 52

Gly Ser Tyr Thr Ser Ser Ser Thr Phe Glu Val
1               5                   10

<210> SEQ ID NO 53
<211> LENGTH: 122
<212> TYPE: PRT
<213> ORGANISM: Artificial Sequence
<220> FEATURE:
<223> OTHER INFORMATION: 8A heavy chain
<220> FEATURE:
<221> NAME/KEY: SITE
<222> LOCATION: (1)..(32)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(111)
<223> OTHER INFORMATION: CDR3
<220> FEATURE:
<221> NAME/KEY: SITE
<222> LOCATION: (112)..(122)
<223> OTHER INFORMATION: FR4

<400> SEQUENCE: 53

Met Ala Gln Val Gln Leu Val Gln Ser Gly Ala Glu Val Lys Lys Pro
1               5                   10                  15

Gly Ala Ser Val Lys Leu Ser Cys Lys Ala Ser Gly Tyr Thr Phe Ser
                20                  25                  30

Ser Tyr Trp Met His Trp Val Arg Gln Ala Pro Gly Gln Arg Leu Glu
            35                  40                  45

Trp Met Gly Glu Ile Asn Pro Gly Asn Gly His Thr Asn Tyr Asn Glu
```

```
                50                  55                  60
Lys Phe Lys Ser Arg Val Thr Ile Thr Val Gly Lys Ser Ala Ser Thr
 65                  70                  75                  80

Ala Tyr Met Glu Leu Ser Ser Leu Arg Ser Glu Asp Thr Ala Val Tyr
                 85                  90                  95

Tyr Cys Ala Arg Glu Gly Val Ser Ala Ala Gly Gly Leu Asp His Trp
                100                 105                 110

Gly Gln Gly Thr Gln Ile Thr Val Ser Ser
            115                 120
```

<210> SEQ ID NO 54
<211> LENGTH: 5
<212> TYPE: PRT
<213> ORGANISM: Artificial Sequence
<220> FEATURE:
<223> OTHER INFORMATION: Synthetic peptide

<400> SEQUENCE: 54

```
Ser Tyr Trp Met His
 1               5
```

<210> SEQ ID NO 55
<211> LENGTH: 17
<212> TYPE: PRT
<213> ORGANISM: Artificial Sequence
<220> FEATURE:
<223> OTHER INFORMATION: Synthetic peptide

<400> SEQUENCE: 55

```
Glu Ile Asn Pro Gly Asn Gly His Thr Asn Tyr Asn Glu Lys Phe Lys
 1               5                  10                  15

Ser
```

<210> SEQ ID NO 56
<211> LENGTH: 11
<212> TYPE: PRT
<213> ORGANISM: Artificial Sequence
<220> FEATURE:
<223> OTHER INFORMATION: Synthetic peptide

<400> SEQUENCE: 56

```
Glu Gly Val Ser Ala Ala Gly Gly Leu Asp His
 1               5                  10
```

<210> SEQ ID NO 57
<211> LENGTH: 108
<212> TYPE: PRT
<213> ORGANISM: Artificial Sequence
<220> FEATURE:
<223> OTHER INFORMATION: 8A light chain
<220> FEATURE:
<221> NAME/KEY: SITE
<222> LOCATION: (1)..(23)
<223> OTHER INFORMATION: FR1
<220> FEATURE:
<221> NAME/KEY: SITE
<222> LOCATION: (24)..(34)
<223> OTHER INFORMATION: CDR1
<220> FEATURE:
<221> NAME/KEY: SITE
<222> LOCATION: (35)..(49)
<223> OTHER INFORMATION: FR2
<220> FEATURE:
<221> NAME/KEY: SITE
<222> LOCATION: (50)..(56)
<223> OTHER INFORMATION: CDR2
<220> FEATURE:
<221> NAME/KEY: SITE

```
<222> LOCATION: (57)..(88)
<223> OTHER INFORMATION: FR3
<220> FEATURE:
<221> NAME/KEY: SITE
<222> LOCATION: (89)..(97)
<223> OTHER INFORMATION: CDR3
<220> FEATURE:
<221> NAME/KEY: SITE
<222> LOCATION: (98)..(108)
<223> OTHER INFORMATION: FR4

<400> SEQUENCE: 57

Asp Ile Gln Met Thr Gln Ser Pro Ser Ser Leu Ser Val Ser Thr Gly
1               5                   10                  15

Ala Arg Val Thr Ile Thr Cys Arg Ala Ser Gln Gly Ile Ser Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg
            100                 105

<210> SEQ ID NO 58
<211> LENGTH: 11
<212> TYPE: PRT
<213> ORGANISM: Artificial Sequence
<220> FEATURE:
<223> OTHER INFORMATION: Synthetic peptide

<400> SEQUENCE: 58

Arg Ala Ser Gln Gly Ile Ser Asn Tyr Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Ala Ala Ser Thr Leu Gln Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Gln Gln Leu Asn Ser Tyr Pro Leu Thr
1               5

<210> SEQ ID NO 61
<211> LENGTH: 120
<212> TYPE: PRT
<213> ORGANISM: Artificial Sequence
<220> FEATURE:
<223> OTHER INFORMATION: 12F heavy chain
```

```
<220> FEATURE:
<221> NAME/KEY: SITE
<222> LOCATION: (1)..(32)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(109)
<223> OTHER INFORMATION: CDR3
<220> FEATURE:
<221> NAME/KEY: SITE
<222> LOCATION: (110)..(120)
<223> OTHER INFORMATION: FR4

<400> SEQUENCE: 61

Met Ala Gln Val Gln Leu Val Gln Ser Gly Ala Glu Val Lys Lys Pro
1               5                   10                  15

Gly Ala Ser Val Lys Leu Ser Cys Lys Ala Ser Gly Tyr Thr Phe Ser
            20                  25                  30

Ser Tyr Trp Met His Trp Val Arg Gln Ala Pro Gly Gln Arg Leu Glu
        35                  40                  45

Trp Met Gly Glu Ile Asn Pro Gly Asn Gly His Thr Asn Tyr Asn Glu
    50                  55                  60

Lys Phe Lys Ser Arg Val Thr Ile Thr Val Asp Lys Ser Ala Ser Thr
65                  70                  75                  80

Ala Tyr Met Glu Leu Ser Ser Leu Arg Ser Glu Asp Thr Ala Val Tyr
                85                  90                  95

Tyr Cys Ala Arg Glu Leu Glu Glu Gly Ala Phe Asp Ile Trp Gly Gln
            100                 105                 110

Gly Thr Met Val Thr Val Ser Ser
        115                 120

<210> SEQ ID NO 62
<211> LENGTH: 5
<212> TYPE: PRT
<213> ORGANISM: Artificial Sequence
<220> FEATURE:
<223> OTHER INFORMATION: Synthetic peptide

<400> SEQUENCE: 62

Ser Tyr Trp Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic peptide

<400> SEQUENCE: 63

Glu Ile Asn Pro Gly Asn Gly His Thr Asn Tyr Asn Glu Lys Phe Lys
1               5                   10                  15
```

Ser

```
<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Glu Leu Glu Glu Gly Ala Phe Asp Ile
1               5

<210> SEQ ID NO 65
<211> LENGTH: 108
<212> TYPE: PRT
<213> ORGANISM: Artificial Sequence
<220> FEATURE:
<223> OTHER INFORMATION: 12F light chain
<220> FEATURE:
<221> NAME/KEY: SITE
<222> LOCATION: (1)..(23)
<223> OTHER INFORMATION: FR1
<220> FEATURE:
<221> NAME/KEY: SITE
<222> LOCATION: (24)..(34)
<223> OTHER INFORMATION: CDR1
<220> FEATURE:
<221> NAME/KEY: SITE
<222> LOCATION: (35)..(49)
<223> OTHER INFORMATION: FR2
<220> FEATURE:
<221> NAME/KEY: SITE
<222> LOCATION: (50)..(56)
<223> OTHER INFORMATION: CDR2
<220> FEATURE:
<221> NAME/KEY: SITE
<222> LOCATION: (57)..(88)
<223> OTHER INFORMATION: FR3
<220> FEATURE:
<221> NAME/KEY: SITE
<222> LOCATION: (89)..(97)
<223> OTHER INFORMATION: CDR3

<400> SEQUENCE: 65

Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Gly Ile Ser Ser Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Val Pro Leu
                85                  90                  95

Thr Phe Gly Gly Gly Thr Lys Val Glu Ile Lys Arg
            100                 105

<210> SEQ ID NO 66
<211> LENGTH: 11
<212> TYPE: PRT
<213> ORGANISM: Artificial Sequence
<220> FEATURE:
<223> OTHER INFORMATION: Synthetic peptide

<400> SEQUENCE: 66
```

Arg Ala Ser Gln Gly Ile Ser Ser Tyr Leu Ala
1               5                   10

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide

<400> SEQUENCE: 67

Ala Ala Ser Thr Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Gln Gln Tyr Asp Ser Val Pro Leu Thr
1               5

<210> SEQ ID NO 69
<211> LENGTH: 121
<212> TYPE: PRT
<213> ORGANISM: Artificial Sequence
<220> FEATURE:
<223> OTHER INFORMATION: 5G4 heavy chain
<220> FEATURE:
<221> NAME/KEY: SITE
<222> LOCATION: (1)..(32)
<223> OTHER INFORMATION: FR1
<220> FEATURE:
<221> NAME/KEY: SITE
<222> LOCATION: (33)..(37)
<223> OTHER INFORMATION: CDR1
<220> FEATURE:
<221> NAME/KEY: SITE
<222> LOCATION: (38)..(51)
<223> OTHER INFORMATION: FR2
<220> FEATURE:
<221> NAME/KEY: SITE
<222> LOCATION: (52)..(68)
<223> OTHER INFORMATION: CDR2
<220> FEATURE:
<221> NAME/KEY: SITE
<222> LOCATION: (69)..(100)
<223> OTHER INFORMATION: FR3
<220> FEATURE:
<221> NAME/KEY: SITE
<222> LOCATION: (101)..(110)
<223> OTHER INFORMATION: CDR3
<220> FEATURE:
<221> NAME/KEY: SITE
<222> LOCATION: (111)..(121)
<223> OTHER INFORMATION: FR4

<400> SEQUENCE: 69

Met Ala Gln Val Gln Leu Val Ser Ser Gly Ala Glu Val Lys Lys Pro
1               5                   10                  15

Gly Ala Ser Val Lys Leu Ser Cys Lys Ala Ser Gly Tyr Thr Phe Ser
            20                  25                  30

Ser Tyr Trp Met His Trp Val Arg Gln Ala Pro Gly Gln Arg Leu Glu
        35                  40                  45

Trp Met Gly Glu Ile Asn Pro Gly Asn Gly His Thr Asn Tyr Asn Glu
    50                  55                  60

```
Lys Phe Lys Ser Arg Val Thr Ile Thr Val Asp Lys Ser Ala Ser Thr
 65                  70                  75                  80

Ala Tyr Met Glu Leu Ser Ser Leu Arg Ser Glu Asp Thr Ala Val Tyr
                 85                  90                  95

Tyr Cys Ala Arg Glu Asp Asp Ile Glu Asp Ala Phe Asp Phe Trp Gly
            100                 105                 110

Gln Gly Thr Met Val Thr Val Ser Ser
        115                 120

<210> SEQ ID NO 70
<211> LENGTH: 5
<212> TYPE: PRT
<213> ORGANISM: Artificial Sequence
<220> FEATURE:
<223> OTHER INFORMATION: Synthetic peptide

<400> SEQUENCE: 70

Ser Tyr Trp Met His
1               5

<210> SEQ ID NO 71
<211> LENGTH: 17
<212> TYPE: PRT
<213> ORGANISM: Artificial Sequence
<220> FEATURE:
<223> OTHER INFORMATION: Synthetic peptide

<400> SEQUENCE: 71

Glu Ile Asn Pro Gly Asn Gly His Thr Asn Tyr Asn Glu Lys Phe Lys
1               5                   10                  15

Ser

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Glu Asp Asp Ile Glu Asp Ala Phe Asp
1               5

<210> SEQ ID NO 73
<211> LENGTH: 108
<212> TYPE: PRT
<213> ORGANISM: Artificial Sequence
<220> FEATURE:
<223> OTHER INFORMATION: 5G4 light chain
<220> FEATURE:
<221> NAME/KEY: SITE
<222> LOCATION: (1)..(23)
<223> OTHER INFORMATION: FR1
<220> FEATURE:
<221> NAME/KEY: SITE
<222> LOCATION: (24)..(34)
<223> OTHER INFORMATION: CDR1
<220> FEATURE:
<221> NAME/KEY: SITE
<222> LOCATION: (35)..(49)
<223> OTHER INFORMATION: FR2
<220> FEATURE:
<221> NAME/KEY: SITE
<222> LOCATION: (50)..(56)
<223> OTHER INFORMATION: CDR2
<220> FEATURE:
<221> NAME/KEY: SITE
<222> LOCATION: (57)..(88)
<223> OTHER INFORMATION: FR3
```

```
<220> FEATURE:
<221> NAME/KEY: SITE
<222> LOCATION: (89)..(97)
<223> OTHER INFORMATION: CDR3
<220> FEATURE:
<221> NAME/KEY: SITE
<222> LOCATION: (98)..(108)
<223> OTHER INFORMATION: FR4

<400> SEQUENCE: 73

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Asn Leu Gln Ser Gly Val Pro Ser Arg Phe Ser Gly
50                  55                  60

Ser Gly Ser Gly Thr Asp Phe Thr Leu Thr Ile Ser Ser Leu His Pro
65                  70                  75                  80

Glu Asp Phe Ala Thr Tyr Phe Cys His Lys Thr Asp Ser Phe Pro Leu
                85                  90                  95

Thr Phe Gly Gly Gly Thr Lys Val Glu Ile Lys Arg
            100                 105

<210> SEQ ID NO 74
<211> LENGTH: 11
<212> TYPE: PRT
<213> ORGANISM: Artificial Sequence
<220> FEATURE:
<223> OTHER INFORMATION: Synthetic peptide

<400> SEQUENCE: 74

Arg Ala Ser Gln Ser Ile Ser Ser Trp Leu Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic peptide

<400> SEQUENCE: 75

Gly Ala Ser Asn Leu Gln Ser
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

His Lys Thr Asp Ser Phe Pro Leu Thr
1               5
```

CD9-SPECIFIC HUMAN ANTIBODIES

CROSS REFERENCE TO RELATED APPLICATIONS

This is the U.S. National Phase of International PCT Application No. PCT/KR2008/006913, filed on Nov. 24, 2008, which was published in English under PCT Article 21(2), which claims the benefit of Korean Patent Application No. 10-2008-0059981, filed Jun. 25, 2008.

TECHNICAL FIELD

The present invention relates to a CD9-specific human antibody, more precisely a human antibody comprising CD9 specific complementarity determining region (CDR) and framework region (FR) and a composition for preventing or treating cancer comprising the said antibody.

BACKGROUND ART

CD9 is a glycoprotein receptor belonging to tetraspanin family having molecular weight about 24-27 kD and is known to regulate signal transduction events playing important roles in development, activity, growth and motility of a cell. In addition, CD9 is known being capable of triggering platelet activation and aggregation which regulate cell attachment (Anton, E. S., et al., *J. Neurosci.* 15:584-595, 1995) and cell migration (Klein-Soyer, C., et al., *Arterioscler Thromb Vasc Biol.* 20:360-369, 2000). Moreover, it is known to be involved in various cellular phenomena such as promotion of muscle cell fusion and myotube maintenance.

Tetraspanin family such as CD9 has 4 trans-membrane segments and N- and C-terminal thereof exists in intracellular side CD9. In this alignment model, two extracellular loops (ECLs) protrude between the $1^{st}$ and the $2^{nd}$ and between the $3^{rd}$ and the $4^{th}$ trans-membrane segments, respectively. Thus, tetraspanins are related to various cellular procedures and their various functions seem to be related to their abilities acting as molecular facilitators. The tetraspanins are known to interact with their partner molecules such as some integrins as well as same tetraspanin family molecules such as CD81 and CD63 and the interaction is so called 'Tetraspanin web' (Radford, K. J., et al., *Biochem. Biophys. Res. Comm.* 222:13-18, 1996; Iwamoto, R., et al.,; Le Naour, F., et al., *Mol. Cell. Proteomics* 5:845-857, 2006).

There is a report that the $2^{nd}$ extracellular loop (ECL2) is important to cell attachment (George, A., et al., Blood 100: 4502-4511, 2002). In addition, there is a report that in other tetraspanin family molecules, ECL2 domain is glycosylated, although in CD9 ECL1 domain is glycosylated and ECL2 of CD9 is important to promote activity of Diphteria toxin receptor (DTR) toward Diphtheria toxin (DT) (Hidetoshi, H., et al. 289:782-790, 2001). Besides the reports, many researchers are interested in the function of ECL2 of CD9, but the function is not understood clearly yet.

With respect to cancer, CD9 is called as "motility-related antigen, MRP-1" and is reported to be related with cell motility and tumor metastasis (Miyake, M. and Hakomori, S., *Biochemistry* 30:3328-3334, 1991). However, it is controversial since regarding the role of CD9 in cancer there are some reports showing contrary results according to type of cancers. For example, decreases of expression of CD9 are reported in colon cancer (Mori, M., et al., *Clin. Cancer Res.* 4:1507-1510, 1998), breast cancer (Miyake, M., et al., *Cancer Res.* 55:4127-4131, 1995), lung cancer (Higachiyama, M., et al., *Cancer Res.* 55:6040-6044, 1995; Funakoshi, T., et al., *Oncogene* 22:674-687, 2003) and pancreatic cancer (Sho, M., et al., *Int. J. Cancer* 79:509-516, 1998) and it is reported that this is associated with invasion, metastasis and poor prognosis of patients. However, there are some reports that expression of CD9 is increased in head and neck squamous cell carcinoma (Erovic, B. M., et al., *Head Neck* 25:848-857, 2003) and stomach cancer (Hori, H., et al., *J. Surg. Res.* 117:208-215, 2004) according to the progression of cancers. These contrary reports draw a deduction that CD9 has tissue-specific aspects. Microarray or immunohistochemistry assays for CD9 in ovarian cancers are reported (Drapkin, R., et al., *Hum Pathol.* 35:1014-1021, 2004; Peters, D. G., et al., *Cancer Epidemiol Biomarkers Prev.* 14:1717-1723, 2005; Houle, C. D., et al., *Gynecol Oncol* 86:69-78, 2002), but no function thereof in ovarian is reported.

Based on the fact that poor prognosis of ovarian cancer patients is related to CD9 over-expression, the present inventors tried to develop a CD9 specific antibody. And as a result, the present inventors completed this invention by confirming that human antibodies 10E4, 11G, 3F3, 8A, 12F and 5G4 recognize CD9 extracellular loop 2 domain (CD9-ECL2) as an epitope and thus strongly bind to CD9, are capable of neutralizing CD9, and inhibiting proliferation, invasion and migration of cancer cells.

DISCLOSURE

Technical Problem

It is an object of the present invention to provide a novel CD9-specific human antibody having CD9 antigen neutralizing effect and in vivo/in vitro anti-cancer activity, and a composition for prevention or treatment of cancer comprising the same.

Technical Solution

To achieve the above object, the present invention provides a CD9-specific human antibody comprising a heavy chain containing heavy chain variable region ($V_H$) comprising HCDR1 having one of the amino acid sequences selected from the group consisting of SEQ. ID. NO: 7, NO: 38, NO: 46, NO: 54, NO: 62 and NO: 70, HCDR2 having one of the amino acid sequences selected from the group consisting of SEQ. ID. NO: 8, NO: 39, NO: 47, NO: 55, NO: 63 and NO: 71, and HCDR3 having one of the amino acid sequences selected from the group consisting of SEQ. ID. NO: 9, NO: 40, NO: 48, NO: 56, NO: 64 and NO: 72 or the fragment thereof; and a light chain containing light chain variable region ($V_L$) comprising LCDR1 having one of the amino acid sequences selected from the group consisting of SEQ. ID. NO: 11, NO: 42, NO: 50, NO: 58, NO: 66 and NO: 74, LCDR2 having one of the amino acid sequences selected from the group consisting of SEQ. ID. NO: 12, NO: 43, NO: 51, NO: 59, NO: 67 and NO: 75, and LCDR3 having one of the amino acid sequences selected from the group consisting of SEQ. ID. NO: 13, NO: 44, NO: 52, NO: 60, NO: 68 and NO: 76 or the fragment thereof.

The present invention also provides a gene encoding the heavy chain of the said human antibody or the fragment thereof and an expression vector containing the gene.

The present invention also provides a gene encoding the light chain of the said human antibody or the fragment thereof and an expression vector containing the gene.

The present invention also provides a transformant prepared by transfecting a host cell with the expression vector containing the gene encoding the heavy chain of the said human antibody or the fragment thereof and the expression vector containing the gene encoding the light chain of the said human antibody or the fragment thereof.

The present invention also provides a method for producing a CD9-specific human antibody by culturing the said transformant.

The present invention also provides a composition comprising the said human antibody for preventing or treating cancer overexpressing CD9.

The present invention also provides a method for preventing or treating cancer overexpressing CD9 containing the step of administering a pharmaceutically effective dose of the said composition to a subject.

The present invention also provides a composition for detecting cancer overexpressing CD9 comprising diagnostically effective dose of the said human antibody, the light chain or the heavy chain of the human antibody or the fragment thereof.

The present invention also provides a method for immunodetection of cancer overexpressing CD9 in vitro containing the step of contacting cancer cells with the composition for detection.

The present invention also provides a method for imaging of cancer overexpressing CD9 containing the step of obtaining images from a subject administered with the composition for detection.

In addition, the present invention provides a method for in vivo treatment of cancer and a method for evaluation of prognosis of a cancer patient under the care by confirming tumor cells after administering the said composition for detection to a subject.

Advantageous Effect

The human antibody of the present invention binds specifically to CD9 by recognizing CD9 extracellular loop 2 domain (CD9-ECL2) as an epitope, has CD9 neutralizing effect and excellent anti-cancer effect on those cancer cell lines overexpressing CD9. Therefore, the antibody of the present invention can be effectively used for diagnosis and treatment of cancer overexpressing CD9.

DESCRIPTION OF DRAWINGS

The application of the preferred embodiments of the present invention is best understood with reference to the accompanying drawings, wherein:

FIG. 1 is a diagram illustrating the result of electrophoresis performed to investigate cloning of CD9-ECL2 domain.

FIG. 2 is a diagram illustrating the result of electrophoresis performed to investigate cloning of CD9-ECL2 domain with Mini-prep product.

FIG. 3 is a diagram illustrating the result of Western blotting of CD9-ECL2 protein expressed in 293E cells.

FIG. 4 is a diagram illustrating the result of electrophoresis performed to confirm CD9-ECL2 purified by protein A column chromatography.

FIG. 5 is a diagram illustrating the result of ELISA performed to investigate increase or decrease of poly scFv-phage after panning.

FIG. 6 is a diagram illustrating the result of electrophoresis performed to confirm BstN1 fingerprinting of scFv mono phage clone.

FIG. 7 is a set of graphs illustrating the result of flow cytometry analysis performed to examine 10E4 antibody binding with two different cancer cell lines:

A: graph showing the results of experiment with ovarian cancer cells (2774); B: graph showing the result of experiment with renal cancer cells (U031); a): ALB6 (anti-CD9) binding strength, Normal mouse IgG was used as the negative control; and b): 10E4 binding strength, #38 mono phage was used as the negative control. At this time, scFV phage was detected by using anti-M13-g8p and FITC conjugated anti-mouse IgG antibody.

FIG. 8 is a set of graphs illustrating the result of flow cytometry analysis performed to examine 10E4 antibody binding with two pancreatic cancer cell lines:

A: graph showing the results of experiment with AsPC-1; B: graph showing the result of experiment with MIA PaCa; a): ALB6 (anti-CD9) binding strength, Normal mouse IgG was used as the negative control; and b): 10E4 binding strength, #38 mono phage was used as the negative control. At this time, scFV phage was detected by using anti-M13-g8p and FITC conjugated anti-mouse IgG antibody.

FIG. 9 is a set of graphs illustrating that ALB6 and 10E4 antibodies recognize different sites of CD9 in ovarian cancer cell line:

a) and b): control groups, and b) is the graph illustrating the shift according to ALB6-CD9 binding, confirmed by using mono phage antibody same to competing phage antibody.

FIG. 10 is a diagram illustrating the result of Western blot analysis performed to confirm conversion of 10E4 antibody to whole IgG:

Lane 1 and lane 2 illustrate anti-CD9(10E4) IgG under reduced or not reduced condition, lane 3 and lane 5 illustrate normal human IgG under reduced or not reduced condition, and lane 4 illustrates anti-TMPRSS4(T2-6C) IgG under reduced condition.

FIG. 11 is a diagram illustrating the result of FACS of CD9 in ovarian cancer cell line using 10E4 whole IgG supernatant.

FIG. 12 is a diagram illustrating the inhibition of invasion of ovarian cancer cells by 10E4 human antibody.

FIG. 13 is a diagram illustrating the inhibition of migration of ovarian cancer cells by 10E4 human antibody.

FIG. 14 is a diagram illustrating the inhibition of proliferation of ovarian cancer cells by 10E4 human antibody.

FIG. 15 is a diagram illustrating the result of Western blotting performed to examine different expression patterns of CD9-EC2 specific mutations.

BEST MODE

Hereinafter, the present invention is described in detail.

The present invention provides a CD9-specific human antibody comprising a heavy chain containing heavy chain variable region ($V_H$) comprising HCDR1 having one of the amino acid sequences selected from the group consisting of SEQ. ID. NO: 7, NO: 38, NO: 46, NO: 54, NO: 62 and NO: 70, HCDR2 having one of the amino acid sequences selected from the group consisting of SEQ. ID. NO: 8, NO: 39, NO: 47, NO: 55, NO: 63 and NO: 71, and HCDR3 having one of the amino acid sequences selected from the group consisting of SEQ. ID. NO: 9, NO: 40, NO: 48, NO: 56, NO: 64 and NO: 72 or the fragment thereof; and a light chain containing light chain variable region ($V_L$) comprising LCDR1 having one of the amino acid sequences selected from the group consisting of SEQ. ID. NO: 11, NO: 42, NO: 50, NO: 58, NO: 66 and NO: 74, LCDR2 having one of the amino acid sequences selected from the group consisting of SEQ. ID. NO: 12, NO: 43, NO: 51, NO: 59, NO: 67 and NO: 75, and LCDR3 having one of the amino acid sequences selected from the group consisting of SEQ. ID. NO: 13, NO: 44, NO: 52, NO: 60, NO: 68 and NO: 76 or the fragment thereof.

Preferably, the said human antibody is 1) a CD9-specific human antibody (10E4) comprising a heavy chain containing heavy chain variable region ($V_H$) comprising HCDR1 having the amino acid sequence of SEQ. ID. NO: 7, HCDR2 having the amino acid sequence of SEQ. ID. NO: 8, and HCDR3 having the amino acid sequence of SEQ. ID. NO: 9 or the fragment thereof; and a light chain containing light chain variable region ($V_L$) comprising LCDR1 having the amino acid sequence of SEQ. ID. NO: 11, LCDR2 having the amino acid sequence of SEQ. ID. NO: 12, and LCDR3 having the amino acid sequence of SEQ. ID. NO: 13 or the fragment thereof;

2) a CD9-specific human antibody (11G) comprising a heavy chain containing heavy chain variable region ($V_H$) comprising HCDR1 having the amino acid sequence of SEQ. ID. NO: 38, HCDR2 having the amino acid sequence of SEQ. ID. NO: 39, and HCDR3 having the amino acid sequence of SEQ. ID. NO: 40 or the fragment thereof; and a light chain containing light chain variable region ($V_L$) comprising LCDR1 having the amino acid sequence of SEQ. ID. NO: 42, LCDR2 having the amino acid sequence of SEQ. ID. NO: 43, and LCDR3 having the amino acid sequence of SEQ. ID. NO: 44 or the fragment thereof;

3) a CD9-specific human antibody (3F3) comprising a heavy chain containing heavy chain variable region ($V_H$) comprising HCDR1 having the amino acid sequence of SEQ. ID. NO: 46, HCDR2 having the amino acid sequence of SEQ. ID. NO: 47, and HCDR3 having the amino acid sequence of SEQ. ID. NO: 48 or the fragment thereof; and a light chain containing light chain variable region ($V_L$) comprising LCDR1 having the amino acid sequence of SEQ. ID. NO: 50, LCDR2 having the amino acid sequence of SEQ. ID. NO: 51, and LCDR3 having the amino acid sequence of SEQ. ID. NO: 52 or the fragment thereof;

4) a CD9-specific human antibody (8A) comprising a heavy chain containing heavy chain variable region ($V_H$) comprising HCDR1 having the amino acid sequence of SEQ. ID. NO: 54, HCDR2 having the amino acid sequence of SEQ. ID. NO: 55, and HCDR3 having the amino acid sequence of SEQ. ID. NO: 56 or the fragment thereof; and a light chain containing light chain variable region ($V_L$) comprising LCDR1 having the amino acid sequence of SEQ. ID. NO: 58, LCDR2 having the amino acid sequence of SEQ. ID. NO: 59, and LCDR3 having the amino acid sequence of SEQ. ID. NO: 60 or the fragment thereof;

5) a CD9-specific human antibody (12F) comprising a heavy chain containing heavy chain variable region ($V_H$) comprising HCDR1 having the amino acid sequence of SEQ. ID. NO: 62, HCDR2 having the amino acid sequence of SEQ. ID. NO: 63, and HCDR3 having the amino acid sequence of SEQ. ID. NO: 64 or the fragment thereof; and a light chain containing light chain variable region ($V_L$) comprising LCDR1 having the amino acid sequence of SEQ. ID. NO: 66, LCDR2 having the amino acid sequence of SEQ. ID. NO: 67, and LCDR3 having the amino acid sequence of SEQ. ID. NO: 68 or the fragment thereof; or 6) a CD9-specific human antibody comprising a heavy chain containing heavy chain variable region ($V_H$) comprising HCDR1 having the amino acid sequence of SEQ. ID. NO: 70, HCDR2 having the amino acid sequence of SEQ. ID. NO: 71, and HCDR3 having the amino acid sequence of SEQ. ID. NO: 72 or the fragment thereof; and a light chain containing light chain variable region ($V_L$) comprising LCDR1 having the amino acid sequence of SEQ. ID. NO: 74, LCDR2 having the amino acid sequence of SEQ. ID. NO: 75, and LCDR3 having the amino acid sequence of SEQ. ID. NO: 76 or the fragment thereof;

The variable region herein indicates a region of an antibody molecule which specifically binds to an antigen and demonstrates modifications in sequence, which is exemplified by CDR1, CDR2 and CDR3. Complementarity determining region (CDR) indicates a loop involved in antigen recognition. Specificity of an antibody to antigen depends on modification in that region. Between CDRs, there is the framework region (FR) which supports the CDR loop.

The antibody herein includes not only a whole antibody but also a functional fragment of the antibody molecule. The whole antibody comprises two full length light chains and two full length heavy chains. Each light chain is linked to heavy chain by disulfide bond. The functional fragment indicates a fragment maintains antigen binding function. Here are the examples of such antibody fragments; (i) Fab fragment composed of light chain variable region ($V_L$), heavy chain variable region ($V_H$), light chain constant region (CL), and heavy chain $1^{st}$ constant region (CH1); (ii) Fd fragment composed of VH and CH1; (iii) Fv fragment composed of Vl and VH of a monoclonal antibody; (iv) dAb fragment composed of VH domain [(Ward, E. S. et al., Nature 341: 544-546 (1989)]; (v) separated CDR region; (vi) F(ab')2 fragment composed of two linked Fab fragments; (vii) single chain Fv molecule (scFv) composed of VH domain and VL domain linked by a peptide linker to form an antigen binding site; (viii) non-specific single chain Fv dimer (PCT/US92/09965); and (ix) polyvalent or multi-specific diabody fragment (WO94/13804) prepared by gene fusion.

In this invention, a CD9-specific human antibody was obtained as scFv by using phage display technology and screened as a mono phage clone. As a result, CD9-specific 10E4, 11G, 3F3, 8A, 12F and 5G4 phage clones were obtained.

The present inventors first constructed library phage from human naive scFv library cells having diversity. Then, the present inventors prepared and purified CD9-ECL2 protein to screen CD9 extracellular loop 2 domain (CD9-ECL2) specific antibody (see FIGS. 1-4). Next, the prepared library phage was added to the immune tube coated with CD9-ECL2, followed by panning and screening of mono clones strongly binding to CD9-ECL2 (see FIG. 5). The selected mono clones were confirmed by fingerprinting (see FIG. 6), followed by sequencing to confirm CDR regions of $V_H$ and $V_L$ of the antibody (see SEQ. ID. NO: 6, NO: 10, NO: 37, NO: 41, NO: 45, NO: 49, NO: 53, NO: 57, NO: 61, NO: 65, NO: 69 and NO: 73). Homology between the above antibody and germ line antibody group was investigated by Ig BLAST program of NCBI web-site (http://www.ncbi.nlm.nih.gov/igblast/). As a result, CD9-EC2 specific 10E4, 11G, 3F3, 8A, 12F and 5G4 phage antibodies were obtained.

In this invention, it was confirmed that 10E4 phage antibody, as scFv, was specifically bound to CD9 over-expressed in ovarian cancer, renal cancer, and pancreatic cancer cell lines by phage FACS (see FIGS. 7 and 8). To confirm whether 10E4 phage antibody had the same epitope with ALB6 known as a CD9-specific antibody, investigation was performed by the same manner as described in a reference (Ando T., et al. *Endocrinology* 145 (11): 5185-93, 2004). As a result, these two had different epitopes (see FIG. 9).

To prepare a human antibody for in vivo diagnosis and treatment of cancer, 10E4 monoclonal phage was converted to whole IgG (see FIG. 10) and then CD9 specific binding and neutralizing effect of whole IgG converted from 10E4 were confirmed by FACS (see FIG. 11).

Thus, the human antibody of the present invention was confirmed to be specifically bound to CD9, have different epitope from other CD9 antibodies and have strong CD9 neutralizing effect.

In this invention, it was also investigated whether 10E4 human antibody could inhibit cancer cell lines. 10E4 human antibody (experimental group) and normal human IgG (control) were added to pre-cultured ovarian cancer cell line in invasion medium, migration medium and serum-free medium, followed by culture. Then, the number of cells was counted. As a result, 10E4 human antibody significantly inhibited invasion, migration and proliferation of the cancer cell line, compared with the control group. Therefore, the antibody of the present invention was confirmed to inhibit invasion and migration of ovarian cancer cell line and at the same time to have neutralizing effect on CD9, the ovarian cancer marker (see FIGS. 12 and 13).

The human antibody of the present invention is characterized by recognizing the peptide fragment represented by SEQ. ID. NO: 36 in CD9 extracellular loop 2 domain (CD9-ECL2) as an epitope, but the epitope herein is not limited to the said peptide fragment.

The present inventors investigated whether 10E4 human antibody could recognize epitope in CD9 extracellular loop domain (CD9-ECL2). Different mutant forms of the antigen CD9-ECL2 were prepared (see FIG. 14). Then, 10E4 human antibody was treated to those mutant protein forms. As a result, 10E4 antibody demonstrated weak binding to M1 (186K→D, 190D→H and 191N→S) among many mutant forms of CD9-ECL2. However, unlike 10E4, ALB6 demonstrated strong binding to M1 (see Table 9). In the meantime, both 10E4 and ALB6 demonstrated strong binding to M4. So, ABL6 and 10E4 recognize different epitopes when they recognize CD9, the ovarian cancer target antigen. And 10E4 recognizes the peptide fragment represented by SEQ. ID. NO: 36 (KEVFDN) in CD9-ECL2 as an epitope.

The present invention also provides a gene encoding the heavy chain of the said human antibody or the fragment thereof, and a gene encoding the light chain of the said human antibody or the fragment thereof.

The present invention also provides an expression vector containing a gene encoding the heavy chain of the said human antibody or the fragment thereof or the gene and a gene encoding the constant region of the heavy chain.

The present invention also provides an expression vector containing a gene encoding the light chain of the said human antibody or the fragment thereof or the gene and a gene encoding the constant region of the light chain.

The present invention also provides transformants produced by transfecting host cells with those two expression vectors above.

The host cell herein can be a prokaryotic cell such as *E. coli* or *Bacillus subtilis* or can be an eukaryotic cell originated from yeast such as *Saccharomyces cerevisiae*, an insect cell, a plant cell and an animal cell. A method for introduction of the said expression vector to a host cell can be any conventional method known to those in the art.

The present invention also provides a method for producing a CD9-specific human antibody comprising the following steps:
1) culturing the said transformant; and
2) purifying the human antibody of the present invention from the culture solution.

Herein, the culture medium appropriate for the transformant can be selected among general culture media well known to those in the art. A method for purification of the antibody can also be any conventional method well known to those in the art.

The method for producing a CD9-specific human antibody is preferably composed of the following steps, but not always limited thereto:
1) inducing immune response by administering CD9-ECL2 protein to an animal;
2) obtaining tissues from the immune response induced animal and constructing gene library;
3) constructing phage library by infecting the host cell transfected with the expression vector containing the gene with helper phage;
4) selecting phages expressing anti-CD9 antibody demonstrating strong binding to CD9 with high affinity after biopanning of the phage library;
5) obtaining DNA encoding the antibody from the said phage and constructing an expression vector by operably inserting a region encoding the variable region into a vector containing a gene encoding the constant region of the human antibody;
6) generating a transformant by inserting the vector constructed in step 5) into a host cell, followed by culture thereof; and
7) purifying the antibody from the culture solution. The host cell herein can be a prokaryotic cell such as *E. coli* or *Bacillus subtilis* or can be an eukaryotic cell originated from yeast such as *Saccharomyces cerevisiae*, an insect cell, a plant cell and an animal cell. A method for introduction of the said expression vector into a host cell can be any conventional method known to those in the art.

The present invention also provides a composition comprising the human antibody for preventing and treating cancer overexpressing CD9.

The cancer overexpressing CD9 is exemplified by sqamous cell carcinoma, stomach cancer and ovarian cancer, but not always limited thereto and any cancer overexpressing CD9 can be a target.

The effective dosage of the pharmaceutical composition of the present invention is preferably the serum concentration of an antibody that enables saturation of CD9. The composition contains 10E4, 11G, 3F3, 8A, 12F or 5G4 human antibody or transformants containing the same as an active ingredient and additionally includes one or more effective ingredients having the same or similar functions to the said active ingredient. In addition to the active ingredient, the composition of the present invention can include one or more pharmaceutically acceptable carriers such as saline, sterilized water, Ringer's solution, buffered saline, dextrose solution, maltodextrin solution, glycerol, ethanol, liposome and a mixture comprising one or more of those components. If necessary, a general additive such as an antioxidant, a buffer, and a bacteriostatic agent can be additionally added. The composition of the present invention can be formulated in different forms including aqueous solutions, suspensions and emulsions for injection, pills, capsules, granules or tablets by mixing with diluents, dispersing agents, surfactants, binders and lubricants. A target cell specific antibody or other ligands can be mixed with one of the said carriers to be delivered to the target cell. The composition can further be prepared in suitable forms according to ingredients by following the method represented in Remington's Pharmaceutical Science, Mack Publishing Company, Easton Pa.

The present invention also provides a method for treating cancer overexpressing CD9 containing the step of administering a pharmaceutically effective dose of the said pharmaceutical composition to a subject with cancer.

The present invention also provides a method for preventing cancer overexpressing CD9 containing the step of administering a pharmaceutically effective dose of the said pharmaceutical composition to a subject.

The cancer overexpressing CD9 is exemplified by sqamous cell carcinoma, stomach cancer and ovarian cancer, but not always limited thereto and any cancer overexpressing CD9 can be a target.

The pharmaceutical composition of the present invention can be administered parenterally (for example, intravenous, hypodermic, peritoneal or local injection), and intravenous injection is preferred. In some cases of solid cancer, local administration which favors fast and easy access of antibody is more preferred. The effective dosage of the composition can be determined according to weight, age, gender, health condition, diet, administration frequency, administration method, excretion and severity of a disease. One time dosage of the composition containing chimeric antibody, humanized antibody or transformant approximately 5-500 mg/m$^2$, which can be administered daily or weekly. The dosage of antibody fragment is suggested to be administered more frequently to maintain serum level enough to induce saturation of CD9. The effective dosage can be adjusted by a doctor who treats malignant tumor patients.

The pharmaceutical composition of the present invention can be administered alone or together with surgical operation, hormone therapy, chemo-therapy and biological regulators to treat malignant tumors.

The present invention also provides a composition for detecting cancer overexpressing CD9 comprising diagnostically effective dose of the said human antibody, the light chain or the heavy chain of the human antibody or the fragment thereof.

The said human antibody, the light chain or the heavy chain of the human antibody or the fragment thereof having immunological activity can be directly or indirectly conjugated or linked to one or more detectable markers selected from the group consisting of therapeutic isotopes, fluorescent materials, enzymes, enzyme substrates, coenzymes, enzyme inhibitors and ligands. The isotope herein is preferably exemplified by $^3$H, $^{11}$C, $^{14}$C, $^{18}$F, $^{64}$Cu, $^{76}$Br, $^{86}$Y, $^{99m}$Tc, $^{111}$In, $^{123}$I, $^{177}$Lu, a mixture thereof and a combination thereof.

The present invention also provides a method for immunodetection of cancer overexpressing CD9 in vitro containing the step of contacting cancer cells with the composition for detecting cancer.

The composition for detecting cancer can be conjugated to a solid substrate to facilitate following steps including washing and separation of a complex, etc. The solid substrate herein is exemplified by synthetic resin, nitrocellulose, glass plate, metal plate, glass fiber, microsphere and microbead, etc. The synthetic resin herein is exemplified by polyester, polyvinyl chloride, polystyrene, polypropylene, PVDF and nylon.

The cancer cells can be diluted properly before contact with the composition for detecting cancer.

The present invention also provides a method for imaging of cancer overexpressing CD9 in vivo comprising the following steps:

1) administering diagnostically effective dose of the composition for detecting cancer to a subject; and 2) obtaining detection images of the subject.

The detection images are obtained by near-infrared imaging, PET, MRI or ultrasonic imaging.

The present invention also provides a method for in vivo treatment of cancer overexpressing CD9 comprising the following steps:

1) administering the composition for detecting cancer into a subject by intravenous injection;
2) confirming tumor cells by detecting the composition of step 1); and
3) eliminating the tumor cells confirmed in step 2) by surgical operation.

In addition, the present invention provides a method for evaluation of prognosis of a cancer patient under the care comprising the following steps:

1) administering the composition for detecting cancer into a patient whose tumor has been eliminated by intravenous injection;
2) confirming tumor cells by detecting the composition of step 1); and
3) judging that all tumor cells have been eliminated when tumor cells are not detected in step 2).

[Mode For Invention]

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of Library Phage $2.7 \times 10^{10}$ human naive scFv library cells having diversity were cultured in a medium (3 L) containing 17 g of 2×YTCM [tryptone (CONDA, 1612.00), 10 g of yeast extract (CONDA, 1702.00), 5 g of NaCl (Sigma, S7653-5 kg), 34 ug/ml of chloramphenicol (sigma, C0857)], 2% glucose (Sigma, G5400), and 5 mM MgCl$_2$ (Sigma, M2393) at 37° C. for 2-3 hours (OD$_{600}$=0.5~0.7). Then, the cells were infected with helper phage, followed by culture in a medium containing 17 g of 2×YTCMK [tryptone (CONDA, 1612.00), 10 g of yeast extract (CONDA, 1702.00), 5 g of NaCl (Sigma, S7653-5 kg), 34 ug/ml of (Sigma, C0857)], 70 ug/ml of kanamycin (Sigma, K1876), 5 mM MgCl$_2$, and 1 mM IPTG (ELPISBIO IPTG025) at 30° C. for 16 hours. The cells proceeded to centrifugation (4500 rpm, 15 min, 4° C.) and supernatant was obtained, which was dissolved in a solution supplemented with 4% polyethylene glycol (PEG-Fluka 81253) 6000 and 3% NaCl (Sigma S7653), followed by reaction in ice for 1 hour. The reactant was centrifuged again (8000 rpm, 20 min, 4° C.) The pellet was dissolved in PBS [8 g of 140 mM NaCl (Sigma, S7953-5 kg), 1.15 g of 10 mM Na$_2$HPO$_4$ (Sigma, 57907-dibasic), 0.2 g of 1.8 mM KH$_2$PO$_4$ (Sigma S5655: monobasic), and 0.2 g of 2.7 mM KCl (Sigma, p9541)], which proceeded to centrifugation again (12000 rpm, 10 min, 4° C.) As a result, the supernatant containing library phage was obtained, which was transferred into a new tube and stored at 4° C.

EXAMPLE 2

Preparation of Antigen CD9-ECL (Extracellular Loop) 2 Protein

<1-1> CD9-ECL2 Cloning

The present inventors tried to obtain an antigen in order to screen CD9-extracellular loop 2 (ECL2) specific antibody from the human library constructed in Example 1. First, full-length plasmid DNA of CD9 provided from Samsung Medical Center, Seoul, Korea was used as a template for PCR with ECL2 alone and at this time, 5'-CAGGGGGC-CGTGGGGGCCTCCCACAAGGATGAGGTGAT-3 (SEQ. ID. NO: 1)' was used as a forward primer and 5'-TAGCGGC-CGACGCGGCCAAGATGTGGAATTTATTGTCGA-3 (SEQ. ID. NO: 2)' was used as a reverse primer. The amount of the template for PCR with CD9-ECL2 was 100 ng, and the amount of each primer was 10 pmol. Total reaction volume was 50 ul and the content of Pfu DNA polymerase (2.5 unit/ul) was 0.5 ul. PCR with CD9-ECL2 was performed as follows; predenaturation at 94° C. for 2 minutes, denaturation at 94° C. for 30 seconds, annealing at 59° C. for 30 seconds, polymerization at 72° C. for 30 seconds, 30 cycles from denaturation to polymerization, and final extension at 72° C. for 10 minutes. The PCR product was digested with Sfi I, which was introduced into pYW 600 vector. As a result, pYW600-CD9-ECL2 plasmid comprising CMV I.E enhancer/promoter, reader sequence, CD9-ECL2 gene, 6× His tag, Fc, Myc, and 8× His tag in that order was obtained.

Primer dimer was eliminated from the PCR product by using PCR purification kit (Solgent, Cat. No. SPP02-C200). Particularly, PCRB buffer was added to the PCR product 5 times the total volume of the product, which was then well mixed and transferred in spin column, followed by centrifugation at 12,000 rpm for 30 seconds. The solution flowed down the collection tube, bottom of the column, was discarded. Then, the column was re-loaded in the collection tube, to which 750 ul of WB buffer was added, followed by centrifugation (12,000 rpm, 30 sec). The solution collected in the collection tube was discarded and centrifugation continued for 2 more minutes to eliminate the WB buffer completely. The spin column was transferred into a 1.5 ml sterilized microtube, to which 35 ul of sterilized distilled water was added. The mixture stood at room temperature for 1 minute, followed by centrifugation at 12,000 rpm for 2 minutes to obtain purified PCR product. 2 ul of Sfi I (NEB Cat. No. R0123L, 20 unit/ul), 3 ul of 10× buffer and 15 ul of sterilized distilled water were added to 10 ul of the purified PCR product to make the total volume to be 30 ul. Reaction was induced at 50° C. for 2 hours. Then, 252 by CD9-ECL2 insert was confirmed using 1% agarose gel (FIG. 1).

Upon completion of the PCR, the sample was electrophoresed on 1% agarose gel (50 volt, 1 hour) and stained with EtBr. Equal sized bands were cut out by using hand UV detector. Gel purification was performed by using gel extraction kit (Qiagen Cat. No. 28706). The cut out gel was placed in a sterilized microtube and weighed. QG buffer was added thereto three times the volume, followed by dissolving at 50° C. for 10 minutes. When the gel was completely dissolved, same volume of isopropanol was added thereto, which was loaded in Qiaquick spin column, followed by centrifugation at 12,000 rpm for 30 seconds. The solution fallen down through the column was discarded, followed by centrifugation for 2 more minutes to eliminate the buffer solution PE completely. The solution down-flowed was discarded. Then, the column was re-loaded in the collection tube, to which 750 ul of PE buffer was added, followed by centrifugation (12,000 rpm, 30 sec). The solution collected in the collection tube was discarded and centrifugation continued for 2 more minutes to eliminate the PE buffer completely. The spin column was transferred into a 1.5 ml sterilized microtube, to which 20 ul of sterilized distilled water was added. The mixture stood at room temperature for 1 minute, followed by centrifugation at 12,000 rpm for 2 minutes to obtain purified Sfi I digestion product.

1 ul of 10× ligation buffer, 1 ul of pYW 600 Sfi I digestion product (20 ng/ul), 2 ul of sterilized distilled water, and 1 ul of ligase (Roche Cat. No. 10 716 359001. 1 unit/ul) were added to 5 ul of the Sfi I digestion product to make the total volume to be 10 ul, followed by ligation at room temperature for 1 hour. 10 ul of the ligation mixture was mixed with 100 ul of XL1-blue. The mixture was reacted in ice for 10 minutes, followed by heat shock at 42° C. for 1 minute and 30 seconds. Then, the mixture was put in ice again for 5 minutes. 900 ul of LB medium was added thereto, followed by re-generation at 37° C. for 1 hour. Centrifugation was performed at 12,000 rpm for 30 seconds. Total cells were spreaded on LB-Amp plate. On the next day, colonies were confirmed and then mini-prep was performed.

The prepared transformant was cultured in 2 ml of LB-Amp medium, and then transferred into a 1.8 ml microtube, followed by centrifugation at 12,000 rpm for 30 seconds to make the cells down. Mini prep was performed with those cells by using mini-prep kit (Nucleogen Cat. No. 5112). The cells were resuspended in 250 ul of cell resuspension solution, to which 250 ul of cell lysis buffer was added, followed by inverting five times. After standing at room temperature for 1 minute, 350 ul of neutralizing buffer was added thereto, followed by inverting 5 times again. The reactant was centrifuged at 12,000 rpm for 10 minutes at 4° C. to down the tangled protein. The supernatant was transferred in spin column, followed by centrifugation at 12,000 rpm for 30 seconds. The solution down-flowed was discarded. Then, the column was re-loaded in the collection tube, to which 750 ul of washing buffer was added, followed by centrifugation (12,000 rpm, 30 sec). The solution collected in the collection tube was discarded and centrifugation continued for 2 more minutes to eliminate the washing buffer completely. The spin column was transferred into 1.5 ml sterilized microtube, to which 50 ul of sterilized distilled water was added. The mixture stood at room temperature for 1 minute, followed by centrifugation at 12,000 rpm for 2 minutes. The obtained mini-prep product was digested with Sfi I by 5 ul each and cloning was confirmed on 1% agarose gel (FIG. 2). The result of sequencing is as follows:

(SEQ. ID. NO. 3)
MGWSYIILFLVATATDVHSQGAVGASHKDEVIKEVQEFYKDTYNKLKTK

DEPQRETLKAIHYALNCCGLAGGVEQFISDICPKKDVLETFTVKSCPDA

IKEVFDNKFHILAASAASHHHHHHSGLVPRGSDKTHTCPPCPAPELLGG

PSVFLFPPKPKDTLMISRTPEVTCVVVDVSHEDPEVKFNWYVDGVEVHN

AKTKPREEQYNSTYRVVSVLTVLHQDWLNGKEYKCKVSNKALPAPIEKT

ISKAKGQPREPQVYTLPPSRDELTKNQVSLTCLVKGFYPSDIAVEWESN

GQPENNYKTTPPVLDSDGSFFLYSKLTVDKSRWQQGNVFSCSVMHEALH

NHYTQKSLSLSPGKEQKLISEEDLNSAVDHHHHHHHH**.

<2-2> Transfection and Obtainment of Expression Supernatant

The present inventors distributed 293E cells in 5 plates at the density of 2×10$^7$ cells/150 mm dish, followed by culture in a 37° C. CO$^2$ incubator for 16-20 hours. When cell confluency reached 70-80%, transfection was performed. For the transfection, 20 ug of CD9-ECL2 DNA (538 ug/ul) and 40 ug of PEI (polyethylenimine M.W~25,000, Polysciences, Inc. . . . Cat. No. 23966, 2 mg/ml) were mixed in DMEM (Dulbecco's Modified Eagle's Medium, Biowhittaker (Lonza) Cat. No, 12-604F, No FBS), which stood at room temperature for 20 minutes. 20 minutes later, the mixture was dropped on the plate covered with 293E cells, followed by shaking well. A day later, the cells were washed, to which DMEM (No FBS) was added. Supernatant was obtained every 2-3 days. The obtained supernatant was centrifuged at 2,000 rpm for 5 minutes to eliminate cell debris. The supernatant was filtered by using Top-Filter (Millipore Cat. No. SCGP T05 RE), followed by purification. The filtered supernatant was 450 ml in total volume.

Each supernatant obtained every 2-3 days was loaded by 24 ul each at 100 V for 2 hours, and then transferred to NC membrane (Millipore Cat. No. HATF00010) at 85V for 2 hours. The membrane finished with transfer was blocked by using blocking buffer (4% skim milk in TEST) at room temperature for 1 hour. A-His-HRP (Sigma, Cat. No. A7058) was diluted with blocking buffer (4% skim milk in TBST) at 1:4000 and binding was induced at room temperature for 1 hour. The membrane was washed with TBST 5 times every 10 minutes, followed by development (Intron, Cat. No. 12145). Proteins secreted were examined. As a result, it was confirmed that enough amount of CD9-ECL2 was secreted (FIG. 3).

<2-3> Purification of CD9-EC2

To use the CD9-ECL2 obtained in Example <2-2> as an antigen, the present inventors first obtained enough amount of the protein and purified the same. Purification was performed as follows. First, Econo-column (Bio-Rad Cat. No 737-1006, 1×5 cm) was washed with PBS, followed by packing with 500 ul of Protein A (Amersham Cat. No. 17-1279-30). During the packing, 100 ml of PBS (pH 7.4) was spilled to wash beads. And 30 ml of binding buffer (20 mM sodium phosphate buffer (pH 7.0)) was spilled. Then, the obtained supernatant was spilled at the speed of 0.5 ml/min by using Peri-start pump (Bio-Rad Cat. No. 731-8142), leading to binding. After washing with PBS at the speed of 2 ml/min for 1 hour, elution was performed with 500 ul of 0.1 M glycine-HCl (pH2.5). $^1/_{10}$ volume of 1 M Tris-HCl (pH 9.0) was added for neutralization. Among 6 elution fractions, the protein was mainly eluted in #1 and #2 fractions. These two fractions were put in 10 K dialysis membrane, followed by o/n dialysis in 4 L of PBS. All the above processes were performed in a 4° C. cold room. The product was stored at −70° C. by aliquot. After purification, the product was confirmed on 10% SDS-PAGE gel (FIG. 4).

EXAMPLE 3

Construction of CD9-ECL2 Antibody

<3-1> Panning

An immunosorb tube (Nunc 470319) was coated with 50 ug of CD9-ECL2(CD9 extracellular domain 2)-Fc antigen using 4 ml of coating buffer [1.59 g of $Na_2CO_3$ (Sigma, S7795), 2.93 g of $NaHCO_3$ (Sigma, S8875), 0.2 g of $NaN_3$ (Sigma, S2002)] at 4° C. for 16 hours with rotator. Then, the antigen was dissolved in PBS at room temperature for 2 hours, followed by blocking in the immunotube using skim milk [(BD,232100)-4% in 1× PBS]. 2 ml of library phage was added to the immunotube, followed by reaction at room temperature for 2 hours. The immunotube was washed 5 times with PBST (0.05%) and twice with PBS. After washing, antigen specific scFV-phage was eluted using 100 mM TEA (Sigma T-0886). E. coli was transfected with the eluted phage, followed by amplification. The phage amplified at the first panning was washed 13 times with PBST [140 mM NaCl (Sigma, S7953-5 kg) 8 g, 10 mM $Na_2HPO_4$ (Sigma, S7907-dibasic) 1.15 g, 1.8 mM $KH_2PO_4$ (Sigma, S5655-500 g: monobasic) 0.2 g, 2.7 mM KCl 0.2 g (Sigma, p9541), Tween20 (Sigma, p1379) 0.05%] and 23 times with PBS, followed by $2^{nd}$-$4^{th}$ panning by the same manner as described above except that washing times were increased.

As a result, as shown in Table 1, at the $4^{th}$ panning, colony titer against the antigen was increased at least 100 times (Table 1).

TABLE 1

Increase of anti-CD9-Fc phage number through 4 pannings

| Target antigen | Panning | Input phage number | Binding phage number |
|---|---|---|---|
| CD9-ECL2-Fc | $1^{st}$ | $3.2 \times 10^{13}$ | $2.4 \times 10^7$ |
| | $2^{nd}$ | $1.1 \times 10^{13}$ | $1 \times 10^6$ |
| | $3^{rd}$ | $2.3 \times 10^{13}$ | $1.2 \times 10^7$ |
| | $4^{th}$ | $1.3 \times 10^{13}$ | $3 \times 10^9$ |

<3-2> Screening of Phage Antibody

Cell stocks obtained from the $1^{st}$-$4^{th}$ pannings and stored as frozen were dissolved in a medium containing 5 ml of 2× YTCM, 2% glucose, and 5 mM $MgCl_2$ to make $OD_{600}$ as 0.1. Then, the cells were cultured at 37° C. for 2-3 hours ($OD_{600}$=0.5~0.7), which were infected with M1 helper phage. Then, the cells were cultured in a medium containing 2× YTCMK, 5 mM $MgCl_2$ and 1 mM IPTG at 30° C. for 16 hours. The cultured cells were centrifuged (4500 rpm, 15 min, 4° C.), and the supernatant was transferred into a new tube ($1^{st}$~$4^{th}$ panning poly scFv-phage). A 96-well immuno-plate (NUNC 439454) was coated with CD9-EC2-Fc antigen (0.1 μg/well) using coating buffer at 4° C. for 16 hours, followed by blocking with skim milk dissolved in PBS (4%). Each well of the 96-well immuno-plate was washed with 0.2 ml of PBS-tween20 (0.05%). 100 ul of the $1^{st}$-$4^{th}$ panning poly scFV-phage was added to each well, followed by reaction at room temperature for 2 hours. Each well was washed four times with 0.2 ml of PBS-tween20 (0.05%). The secondary antibody anti-M13-HRP (Amersham 27-9421-01) was diluted at 1:2000, followed by reaction at room temperature for 1 hour. OPD tablet (Sigma 8787-TAB) was added to PC buffer ($C_6H_8O_7H_2O$ (Sigma, C0706) 5.1 g, $Na_2HPO_4$ (Sigma, S7907 7.3 g) to make substrate solution, which was added to each well by 100 ul/well, followed by color development for 10 minutes. was measured by using spectrophotometer (MolecularDevice, USA).

As a result, as shown in FIG. 5, it was confirmed by ELISA that antigen binding capacity was increased in the $3^{rd}$ and $4^{th}$ panning poly scFV-phages (FIG. 5).

Colonies obtained from polyclonal antibodies (the $3^{rd}$-$4^{th}$ panning) having strong binding capacity were cultured in a 96-deep well plate (Bioneer, 90030) containing a medium supplemented with 2× YTCM, 2% glucose and 5 mM $MgCl_2$, 1 ml/well, at 37° C. for 16 hours. The cells were cultured until $OD_{600}$ reached 0.1. 100-200 ul of the culture solution was inoculated in a medium supplemented with 2× YTCM, 2% glucose and 5 mM $MgCl_2$, which was loaded in a 96-deep well plate, followed by culture at 37° C. for 2-3 hours until $OD_{600}$ reached 0.5-0.7. The cells were infected with M1 helper phage (MOI=1:20) and the infected cells were cultured in a medium supplemented with 2× YTCMK, 5 mM $MgCl_2$, and 1 mM IPTG at 30° C. for 16 hours. The cultured cells were centrifuged (4500 rpm, 15 min, 4° C.) and supernatant was obtained, to which 4% polyethylene glycol (PEG) 6000 and 3% NaCl were added. Upon completion of dissolving, reaction was induced in ice for 1 hour. The reactant was centrifuged (8000 rpm. 20 min, 4° C.) and pellet was dissolved in PBS. Centrifugation (12000 rpm, 10 min, 4° C.) was performed again and supernatant was obtained, from which the 3rd and the 4th panning monoclonal scFv phages were obtained. The phage was transferred in a new tube and stored at 4° C.

A 96-well immuno-plate was coated with CD9-EC2-Fc antigen (0.1 μg/well) at 4° C. for 16 hours, followed by blocking with skim milk dissolved in PBS (4%). Each well of the 96-well immuno-plate was washed with 0.2 ml of PBS-tween20 (0.05%). 100 ul of the 3rd-4th panning monoclonal scFV-phage was added to each well, followed by reaction at room temperature for 2 hours. Each well was washed four times with 0.2 ml of PBS-tween20 (0.05%). The secondary antibody anti-M13-HRP was diluted at 1:2000, followed by reaction at room temperature for 1 hour. The plate was washed with 0.2 ml of PBS-tween20 (0.05%), followed by color development. $OD_{490}$ was measured.

As a result, as shown in Table 2 and Table 3, 10 monoclones demonstrating strong antigen binding capacity were obtained (Table 2 and Table 3).

TABLE 2

| Clone name | CD9 | a-myc | Fc | Ratio | Clone name | CD9 | a-myc | Fc | Ratio | Clone name | CD9 | a-myc | Fc | Ratio |
|---|---|---|---|---|---|---|---|---|---|---|---|---|---|---|
| 1A4 | 0.263 | 1.401 | 0.139 | 0.188 | 2A | 0.074 | 0.069 | 0.057 | 1.079 | 3A | 1.725 | 1.089 | 1.671 | 1.584 |
| 1B | 1.396 | 0.699 | 1.537 | 1.997 | 2B | 2.412 | 1.586 | 2.358 | 1.521 | 3B | 0.067 | 0.040 | 0.041 | 1.688 |
| 1C | 1.549 | 0.723 | 1.742 | 2.141 | 2C | 0.541 | 1.877 | 0.174 | 0.288 | 3C | 1.835 | 1.020 | 1.718 | 1.800 |
| 1D | 1.302 | 1.628 | 0.849 | 0.799 | 2D | 2.003 | 0.959 | 1.446 | 2.088 | 3D | 1.852 | 1.293 | 1.866 | 1.433 |
| 1E | 0.487 | 0.083 | 0.467 | 5.862 | 2E | 2.010 | 1.160 | 1.471 | 1.733 | 3E | 1.527 | 0.955 | 1.797 | 1.600 |
| 1F | 0.188 | 0.061 | 0.279 | 3.064 | 2F | 2.145 | 1.619 | 1.977 | 1.325 | 3F | 0.045 | 0.041 | 0.040 | 1.096 |
| 1G | 1.112 | 0.525 | 1.392 | 2.118 | 2G | 0.045 | 0.042 | 0.041 | 1.075 | 3G | 0.043 | 0.042 | 0.042 | 1.024 |
| 1H | 1.168 | 0.463 | 1.289 | 2.524 | 2H | 2.564 | 1.895 | 2.524 | 1.353 | 3H | 2.118 | 1.494 | 2.082 | 1.418 |
| 4A | 1.978 | 1.278 | 1.846 | 1.548 | 5A | 0.116 | 0.054 | 0.045 | 2.148 | 6A | 1.996 | 1.476 | 1.811 | 1.353 |
| 4B | 0.129 | 0.046 | 0.044 | 2.786 | 5B | 0.079 | 0.173 | 0.042 | 0.457 | 6B | 0.514 | 1.733 | 0.060 | 0.296 |
| 4C | 0.140 | 0.044 | 0.043 | 3.187 | 5C | 2.427 | 1.578 | 2.461 | 1.538 | 6C | 0.134 | 0.046 | 0.044 | 2.934 |
| 4D | 1.566 | 0.618 | 1.511 | 2.532 | 5D | 2.474 | 1.479 | 2.463 | 1.673 | 6D | 0.088 | 0.046 | 0.044 | 1.896 |
| 4E | 0.438 | 1.202 | 0.079 | 0.364 | 5E | 2.431 | 1.524 | 2.322 | 1.595 | 6E | 1.856 | 0.889 | 1.662 | 2.087 |
| 4F | 2.063 | 1.412 | 1.987 | 1.461 | 5F | 2.049 | 1.448 | 1.905 | 1.415 | 6F | 0.061 | 0.042 | 0.044 | 1.444 |
| 4G | 0.679 | 1.830 | 0.080 | 0.371 | 5G | 1.775 | 1.701 | 0.047 | 1.043 | 6G | 2.074 | 1.581 | 1.844 | 1.312 |
| 4H | 0.099 | 1.899 | 0.099 | 0.052 | 5H | 0.054 | 0.047 | 0.042 | 1.161 | 6H | 0.066 | 0.044 | 0.042 | 1.488 |
| 7A | 0.083 | 0.046 | 0.050 | 1.820 | 8A | 2.119 | 1.281 | 2.121 | 1.654 | 9A | 0.674 | 0.170 | 0.523 | 3.969 |
| 7B | 0.851 | 2.000 | 0.212 | 0.425 | 8B | 0.875 | 2.068 | 0.233 | 0.423 | 9B | 0.092 | 0.042 | 0.094 | 2.199 |
| 7C | 0.093 | 0.045 | 0.058 | 2.090 | 8C | 2.160 | 1.456 | 1.955 | 1.483 | 9C | 0.122 | 0.041 | 0.042 | 3.007 |
| 7D | 2.078 | 1.345 | 1.871 | 1.546 | 8D | 2.375 | 1.723 | 2.310 | 1.379 | 9D | 1.989 | 1.335 | 1.850 | 1.490 |
| 7E | 0.054 | 0.041 | 0.041 | 1.310 | 8E | 2.065 | 1.460 | 1.887 | 1.415 | 9E | 2.016 | 1.612 | 1.889 | 1.251 |
| 7F | 0.055 | 0.040 | 0.040 | 1.388 | 8F | 1.020 | 1.518 | 0.703 | 0.672 | 9F | 2.083 | 1.562 | 1.974 | 1.334 |
| 7G | 0.072 | 0.043 | 0.041 | 1.665 | 8G | 0.045 | 0.043 | 0.043 | 1.046 | 9G | 2.125 | 2.310 | 1.829 | 0.920 |
| 7H | 0.059 | 0.048 | 0.046 | 1.227 | 8H | 0.643 | 0.968 | 0.216 | 0.664 | 9H | 0.058 | 0.052 | 0.044 | 1.122 |
| 10A | 0.113 | 0.060 | 0.048 | 1.894 | 11A | 2.301 | 2.450 | 2.167 | 0.939 | 12A | 0.453 | 1.786 | 0.067 | 0.254 |
| 10B | 1.987 | 1.734 | 1.862 | 1.145 | 11B | 2.315 | 1.530 | 2.204 | 1.513 | 12B | 0.075 | 0.048 | 0.045 | 1.568 |
| 10C | 0.175 | 0.069 | 0.139 | 2.550 | 11C | 0.057 | 0.042 | 0.041 | 1.381 | 12C | 0.880 | 1.715 | 0.101 | 0.513 |
| 10D | 2.591 | 1.745 | 2.500 | 1.485 | 11D | 0.065 | 0.045 | 0.047 | 1.458 | 12D | 0.052 | 0.043 | 0.041 | 1.209 |
| 10E4 | 2.393 | 1.660 | 0.073 | 1.441 | 11E | 2.136 | 1.482 | 2.107 | 1.442 | 12E | 1.949 | 1.104 | 1.756 | 1.765 |
| 10F | 2.684 | 1.974 | 2.470 | 1.360 | 11F | 2.176 | 1.363 | 2.036 | 1.596 | 12F | 1.942 | 1.071 | 1.922 | 1.814 |
| 10G | 0.094 | 0.053 | 0.042 | 1.779 | 11G | 1.337 | 0.437 | 1.296 | 3.056 | 12G | 2.077 | 1.069 | 1.969 | 1.943 |
| 10H | 2.0984 | 1.6753 | 2.1957 | 1.252552 | 11H | 0.046 | 0.047 | 0.042 | 0.972 | 12H | 2.139 | 1.534 | 2.132 | 1.394 |

TABLE 3

| Clone name | CD9 | a-myc | Fc | Ratio | Clone name | CD9 | a-myc | Fc | Ratio | Clone name | CD9 | a-myc | Fc | Ratio |
|---|---|---|---|---|---|---|---|---|---|---|---|---|---|---|
| 1A | 0.0686 | 1.0855 | 0.0448 | 0.063197 | 2A | 1.414 | 1.0507 | 0.5543 | 1.345769 | 3A | 0.1442 | 1.4782 | 0.0577 | 0.09755 |
| 1B | 0.0441 | 0.7301 | 0.0416 | 0.060403 | 2B | 0.1793 | 1.1626 | 0.0414 | 0.154223 | 3B | 0.0401 | 0.6428 | 0.0425 | 0.06238 |
| 1C | 0.077 | 0.6518 | 0.0418 | 0.118134 | 2C | 0.0432 | 0.6788 | 0.0405 | 0.063642 | 3C | 1.462 | 1.5391 | 0.0401 | 0.94991 |
| 1D | 0.4977 | 1.8066 | 0.3916 | 0.27549 | 2D | 0.042 | 0.73 | 0.0408 | 0.057572 | 3D | 1.7298 | 1.1929 | 1.8829 | 1.45008 |
| 1E | 0.1841 | 1.1921 | 0.0424 | 0.154433 | 2E | 0.0404 | 0.6304 | 0.0396 | 0.064086 | 3E | 0.04 | 0.5964 | 0.0405 | 0.06707 |
| 1F | 0.0391 | 0.5982 | 0.0415 | 0.065363 | 2F | 0.0481 | 0.7469 | 0.0405 | 0.0644 | 3F | 0.9609 | 1.047 | 0.0394 | 0.91777 |
| 1G | 0.0414 | 0.6091 | 0.042 | 0.067969 | 2G | 0.051 | 0.7773 | 0.0407 | 0.072044 | 3G | 0.0403 | 0.6073 | 0.0428 | 0.06636 |
| 1H | 0.0786 | 0.8598 | 0.0428 | 0.091417 | 2H | 0.0676 | 1.0243 | 0.0417 | 0.065926 | 3H | 0.0612 | 0.7205 | 0.0418 | 0.08494 |
| 4A | 0.0677 | 0.8405 | 0.0441 | 0.080547 | 5A | 0.0431 | 0.7039 | 0.0432 | 0.06123 | 6A | 1.838 | 1.3607 | 2.2222 | 1.35078 |
| 4B | 2.6126 | 2.0811 | 2.4789 | 1.255394 | 5B | 0.0419 | 0.5838 | 0.0409 | 0.071771 | 6B | 2.0602 | 1.4489 | 2.2426 | 1.42191 |
| 4C | 0.0432 | 0.7359 | 0.0414 | 0.058704 | 5C | 0.042 | 1.1148 | 0.0439 | 0.037675 | 6C | 0.6852 | 1.1413 | 0.3877 | 0.60037 |
| 4D | 0.0412 | 0.6693 | 0.0412 | 0.061557 | 5D | 1.4425 | 1.0345 | 1.7212 | 1.394393 | 6D | 1.9566 | 1.3734 | 2.1564 | 1.42464 |
| 4E | 2.0015 | 1.4016 | 1.9986 | 1.428011 | 5E | 0.0486 | 0.6398 | 0.0412 | 0.075961 | 6E | 0.1527 | 1.624 | 0.0401 | 0.09403 |
| 4F | 0.2391 | 2.3774 | 0.9901 | 0.100572 | 5F | 0.0715 | 0.9691 | 0.0426 | 0.07378 | 6F | 0.1545 | 0.7383 | 0.2532 | 0.20926 |
| 4G | 1.9504 | 1.3583 | 2.1046 | 1.435913 | 5G | 0.0419 | 0.6551 | 0.0415 | 0.06396 | 6G | 0.129 | 1.2391 | 0.0435 | 0.10411 |
| 4H | 0.8374 | 1.7678 | 0.0989 | 0.473696 | 5H | 0.0503 | 0.9116 | 0.0417 | 0.055178 | 6H | 0.7741 | 1.441 | 0.0444 | 0.5372 |
| 7A | 0.1568 | 1.2748 | 0.0458 | 0.123 | 8A | 1.6146 | 2.2122 | 0.088 | 0.729862 | 9A | 0.0485 | 0.6798 | 0.0426 | 0.07134 |
| 7B | 0.0552 | 0.7609 | 0.0413 | 0.072546 | 8B | 0.2503 | 1.5073 | 0.0445 | 0.166059 | 9B | 0.5044 | 1.7549 | 0.0438 | 0.28742 |
| 7C | 0.1212 | 1.2105 | 0.058 | 0.100124 | 8C | 0.1917 | 1.4737 | 0.0452 | 0.130081 | 9C | 0.4488 | 1.0983 | 0.0423 | 0.40863 |
| 7D | 0.0478 | 0.5811 | 0.0515 | 0.082258 | 8D | 2.0597 | 1.2702 | 2.0672 | 1.621556 | 9D | 2.2706 | 1.7955 | 2.4169 | 1.26461 |
| 7E | 0.0821 | 0.8104 | 0.0401 | 0.101308 | 8E | 0.0449 | 0.6071 | 0.0395 | 0.073958 | 9E | 2.5058 | 1.7522 | 2.4991 | 1.43009 |

TABLE 3-continued

| Clone name | CD9 | a-myc | Fc | Ratio | Clone name | CD9 | a-myc | Fc | Ratio | Clone name | CD9 | a-myc | Fc | Ratio |
|---|---|---|---|---|---|---|---|---|---|---|---|---|---|---|
| 7F | 0.0446 | 0.5646 | 0.0449 | 0.078994 | 8F | 1.7202 | 1.1531 | 1.7443 | 1.491805 | 9F | 0.0451 | 1.7476 | 0.0402 | 0.02581 |
| 7G | 0.1574 | 0.6658 | 0.0427 | 0.236407 | 8G | 0.2261 | 1.9721 | 0.0721 | 0.114649 | 9G | 0.2768 | 2.0918 | 0.0735 | 0.13233 |
| 7H | 0.0632 | 0.8462 | 0.0433 | 0.074687 | 8H | 0.0645 | 0.8063 | 0.0444 | 0.079995 | 9H | 0.0405 | 0.644 | 0.0405 | 0.06289 |
| 10A | 0.0608 | 1.0715 | 0.0502 | 0.056743 | 11A | 0.0522 | 0.9812 | 0.0449 | 0.0532 | 12A | 0.083 | 0.8244 | 0.0508 | 0.10068 |
| 10B | 0.0508 | 0.6154 | 0.0413 | 0.082548 | 11B | 0.369 | 0.7231 | 0.5231 | 0.510303 | 12B | 1.7084 | 2.3746 | 1.516 | 0.71945 |
| 10C | 0.2328 | 0.7726 | 0.0415 | 0.30132 | 11C | 0.1887 | 1.6802 | 0.0433 | 0.112308 | 12C | 1.7296 | 2.1705 | 0.6746 | 0.79687 |
| 10D | 0.4881 | 2.2405 | 0.1388 | 0.217853 | 11D | 0.0766 | 0.6154 | 0.0726 | 0.124472 | 12D | 2.6899 | 2.1121 | 2.588 | 1.27357 |
| 10E | 1.783 | 1.7307 | 0.0159 | 1.030219 | 11E | 0.4848 | 2.2758 | 0.1105 | 0.213024 | 12E | 0.9019 | 0.8788 | 0.4712 | 1.02629 |
| 10F | 0.145 | 1.1429 | 0.0416 | 0.12687 | 11F | 2.1933 | 1.68 | 2.2407 | 1.305536 | 12F | 1.1597 | 1.7346 | 0.1239 | 0.66857 |
| 10G | 0.0522 | 0.6942 | 0.0458 | 0.075194 | 11G | 2.2368 | 1.8154 | 0.0441 | 1.232125 | 12G | 0.686 | 1.4588 | 0.4489 | 0.47025 |

<3-3> Separation of Monoclonal Phages and Examination Thereof

Colony PCR was performed with 1 ul of the 10 monoclone cells selected in Example <3-2>, 0.2 ul of Taq DNA polymerase (Gendocs, Korea) (5 U/ul), 10 pmol/ul of each forward primer [(5'-CTAGATAACGAGGGCAAATCATG-3 (SEQ. ID. NO: 4)'] and reverse primer [(5'-CGTCACCAAT-GAAACCATC-3 (SEQ. ID. NO: 5)'], 3 ul of 10× buffer, 0.6 ul of 10 mM dNTP mix, 0.2 ul of pelB (50 p/ul), 0.2 ul of cla3 (50 p/ul) and 24.8 ul of distilled water (iCycler iQ, BIO-RAD). PCR conditions are as shown in Table 4.

TABLE 4

| Temperature | Time | Cycle |
|---|---|---|
| 95° C. | 5 min | |
| 95° C. | 30 sec | 30 |
| 56° C. | 30 sec | |
| 72° C. | 1 min | |
| 72° C. | 10 min | |
| 4° C. | | |

The colony PCR product was confirmed on 1% agarose gel (Seakem L E, CAMERES 50004). 0.2 ul of BstNI (Roche11288075001, 10 U/ul) was taken, followed by reaction at 37° C. for 2-3 hours. Reaction conditions are as shown in Table 5.

TABLE 5

| 10X Buffer | 3 ul |
|---|---|
| colony PCR product | 10 ul |
| BstNI (10 U/ul) | 0.2 ul |
| Distilled water | 16.8 ul |

As a result, fragments of monoclonal phage antibodies digested by BstNI were proved to have diversity on 8% DNA polyacrylamide gel [30% acrylamide (Bio-RAD, 161-0156) 2.66 ml, 10× TBE 1 ml, dH$_2$O 6.27 ml, 10% APS (Sigma, A3678) 70 ul, and TEMED (Bio-RAD, 161-0801) 7 ul] and 6 kinds of monoclonal phage antibodies were confirmed (FIG. 6).

Sequence analysis was performed with monoclonal phage clones confirmed by fingerprinting by BstN1. To do so, monoclonal cells were first cultured in a medium (5 ml) supplemented with 2×YTCM, 2% glucose, and 5 mM MgCl$_2$ at 37° C. for 16 hours. DNA-prep was performed with the cultured monoclonal cells using DNA-prep kit (Nuclogen 5112) to obtain DNA. Sequencing of the DNA was performed by using pelB5 primer [5'-CTAGATAACGAGGGCAAAT-CATG-3 (SEQ. ID. NO: 4)'] (Solgent, Korea). As a result, CDR regions of V$_H$ and V$_L$ of selected antibodies were confirmed.

Homology between the said antibody and germ line antibody family was investigated by Ig BLAST program of NCBI web page (http://www.ncbi.nlm.nih.gov/igblast/). As a result, as shown in Table 6, 5 CD9-EC2 specific phage antibodies were obtained (Table 6).

TABLE 6

| Clone Name | VH | Identities | VL | Identities | VH(CDR3-a.a seq) | Vk(CDR3-a.a seq) | Group | Ratio |
|---|---|---|---|---|---|---|---|---|
| 11G3 | | | L12a | 269/283(95.05%) | DNSPPRI | QQYSDYWT | 1 | 1.2321 |
| 12F3 | VH1-6 | 243/296(83.4%) | L8 | 271/279(97.13%) | EDDIEDAFDF | QQYDSVPLT | 2 | 0.6685 |
| 3F3 | VH1-6 | 243/296(82.1%) | V1-4 | 283/297(95.29%) | DNSPPRI | GSYTSSSTFEV | 3 | 0.9177 |
| 8A3 | VH1-6 | 243/296(82.8%) | L8 | 274/286(95.80%) | EGVSAAGGLDH | QQLNSYPLT | 4 | 0.7298 |
| 5G4 | VH1-6 | 243/296(82.8%) | L8 | 273/284(96.13%) | EDDIEDAFDF | HKTDSFPLT | 5 | 1.043 |
| 10E4 | VH3-9 | 271/287(94.43%) | L8 | 276/286(96.50%) | SPVGTTYFDY | QQLNIFPLT | 6 | 1.441 |

As shown in FIG. 7, phage FACS was performed to select 10E4 phage antibody specifically recognizing and binding to CD9 in ovarian cancer cell line and renal carcinoma cell line overexpressing CD9 like the commercial ALB6 (Beckman coulter) antibody, known as a CD9-specific antibody (FIG. 7). Sequences of the 5 phage antibodies including the CD9-specific 10E4 are as follows:

```
CD9 10E4 HC:
                                       (SEQ. ID. NO: 6)
MAQVQLVQSGGGLVQPGRSLRLSCAASGFTFD DFAMH
WVRQAPGKGLEWVA GISWNSGDIRYADSVRG
RFTISRDNAKNSLFLQMNSLRAEDTAVYYCAR SPVGTTYFDYW
GQGALITVSS,
and
```

```
-continued
CD9 10E4 LC:
                                      (SEQ. ID. NO: 10)
DIQMTQSPSSLSASVGDRVTITC RASQGISSYLA
WYQQKPGKAPKLLIY AASTLQS EVPSRFSGSGSGTDFTLTI
SSLQPEDFATYYC QQLNIFPLT FGGTKVDIKR.

CD9 11G HC:
                                      (SEQ. ID. NO: 37)
MAQVQLVQSGAEVKKPGASVKLSCKASGYTSS SYWMH
WVRQAPGQRLEWMG EINPGNGHTNYNEKFKS
RVTITVDKSASTAYMELSSLRSEDTAVYYCGQDNSPPRI WGQGTL
VTVSS

CD9 11G LC:
                                      (SEQ. ID. NO: 41)
DIQMTQSPSTLSASVGDRVTITC RASQTIGNLA
WFQQKPGKAPKLLIY KASSLES GVPSRFSGSGSGTEFTLTI
SSLQPDDFATYYC QQYSDYWT FGQGTKVEIKR

CD9 3F3 HC:
                                      (SEQ. ID. NO: 45)
MAQMQLVQSGAEVKKPGASVKLSCKASGYTFS SYWMH
WVRQAPGQRLEWMG EINPGNGHTNYNEKFKS
RVTITVDKSASTAYMELSSLRSEDTAVYYCGQDNSPPRI WGQGTL
ITVSS

CD9 3F3 LC:
                                      (SEQ. ID. NO: 49)
QSALTQPASVSGSPGQSITISC TGTSSDVGGYNHVS
WYQQHPGKAPKLLIY DVSNRPS GVSGRFSGSKSGNTASLTISGL
QAEDEANYYC GSYTSSSTFEV FGTGTKVTVLR

CD9 8A HC:
                                      (SEQ. ID. NO: 53)
MAQVQLVQSGAEVKKPGASVKLSCKASGYTFS SYWMH
WVRQAPGQRLEWMG EINPGNGHTNYNEKFKS
RVTITVGKSASTAYMELSSLRSEDTAVYYCAREGVSAAGGLDH
WGQGTQITVSS

CD9 8A LC:
                                      (SEQ. ID. NO: 57)
DIQMTQSPSSLSVSTGARVTITC RASQGIS NYLA
WYQQKPGKAPKLLIY AASTLQS GVPSRFSGSGSGTDFTLTI
SSLQPEDFATYYC QQLNSYPLT FGGGTKVEIKR

CD9 12F HC:
                                      (SEQ. ID. NO: 61)
MAQVQLVQSGAEVKKPGASVKLSCKASGYTFS SYWMH
WVRQAPGQRLEWMG EINPGNGHTNYNEKFKS
RVTITVDKSASTAYMELSSLRSEDTAVYYCARELEEGAFDI WGQG
TMVTVSS

CD9 12F LC:
                                      (SEQ. ID. NO: 65)
DIQMTQSPSSLPASVGDRVTITC RASQGISSYLA
WYQQKPGKAPKLLIY AASTLQS GVPSRFSGSGSGTDFTLTI
SSLQPEDFATYYC QQYDSVPLT FGGGTKVEIKR

CD9 5G4 HC:
                                      (SEQ. ID. NO 69)
MA QVQLVSSGAEVKKPGASVKLSCKASGYTFS SYWMH
WVRQAPGQRLEWMG EINPGNGHTNYNEKFKS
RVTITVDKSASTAYMELSSLRSEDTAVYYCAREDDIEDAFDF
WGQGTMVTVSS

CD9 5G4 LC:
                                      (SEQ. ID. NO: 73)
DIQMTQSPSSVSASVGDRVTITC RASQSISSWLA
WYQQKPGKAPKLLIY GASNLQS GVPSRFSGSGSGTDFTLTI
SSLHPEDFATYFC HKTDSFPLT FGGGTKVEIKR
```

EXAMPLE 4

Investigation of Characteristics of Human Antibody 10E4

<4-1> Phage FACS

The present inventors washed cells in 100 mm plate twice with PBS, to which dissociation buffer-enzyme free PBS based (Gibco, USA) was added, followed by culture at 37° C. for 10 minutes. The cultured cells were collected by using a scraper, followed by centrifugation at 1300 rpm for 3 minutes to obtain pellet. The cells were washed with 2% PBF (1× PBS containing 2% FBS) by the same manner as described in the above, followed by resuspension in 2% PBF. The number of cells was counted and cells for FACS were prepared ($5 \times 10^5$ cells/sample). 100 ul of phage antibody solution or phage antibody 10 fold-concentrated with PEG was added to each sample, followed by reaction in ice for 1 hour. Centrifugation was performed at 1300 for 3 minutes at 4° C. to remove supernatant. 200 ul of 2% PBF solution was added thereto, followed by washing three times by the same manner as described in the above. 100 ul of anti-g8p antibody (Abcam, UK) diluted in 2% PBF solution at 1:200 was added thereto and well mixed, followed by reaction in ice for 30 minutes. Then, centrifugation was performed at 1300 rpm for 3 minutes at 4° C. to eliminate supernatant. 200 ul of 2% PBF solution was added thereto, followed by washing three times by the same manner as described in the above. 100 ul of FITC-conjugated anti-mouse IgG diluted in 2% PBF at 1:1000 was added to each sample, and well mixed, followed by reaction in ice for 30 minutes. 500 ul of 2% PBF solution was added thereto and then the mixture was transferred in FACS tubes (Falcon, USA), followed by mixing using vortex. The stained cells were examined by flow cytometer (Beckman Coulter, USA). The mono phage antibody #38 specifically binding to different antigens each time was treated to a sample at the same concentration, which was used as the internal control. Data analysis was performed by using WINMDI2.9 software.

From the results of FACS, it was confirmed that the antibody of the present invention specifically binds to CD9 overexpressing cancer cell lines such as ovarian adenocarcinoma cell line 2774 and renal carcinoma cell line UO31, like ALB6. As shown in FIG. 8, 10E4, the antibody as scFv, binds specifically and selectively to the target antigen CD9 of pancreatic cancer cell lines (FIG. 8).

<4-2> Examination of epitope in 2774 cells using ALB6 and 10E4

To investigate whether the epitope of ALB6 known as a CD9-specific antibody was same as that of 10E4 selected from human library, the present inventors performed experiment modified from that described in a reference (Ando T., et al. *Endocrinology* 145 (11): 5185-93, 2004). Particularly, FACS was performed to investigate shift of them to confirm whether epitopes of those two antibodies were same. 10E4 phage form before being converted to IgG was used for the experiment and all the processes were performed by the same manner as described in Example <4-1> (Phage FACS). As shown in FIG. 9, 2774 cells were conjugated with ALB6 together with 10E4 diluted at different concentrations. As a result, there was no change in shift in the control (red), suggesting that they recognize different epitopes. So, it was confirmed that those two antibodies have different epitopes against antigen (FIG. 9).

<4-3> Whole IgG Conversion

To construct a human antibody for in vivo diagnosis and treatment of cancer, the present inventors converted CD9 10E4 monoclonal phage to whole IgG. For the conversion, colony PCR was performed (iCycler iQ, BIO-RAD) to obtain the heavy chain using 1 ul of monoclonal DNA, 10 pmole/ul of a heavy chain forward primer [NATVH1-1: 5'-TTGGTG-GCCACAGCGGCCGATGTCCACTCGCAG-GTGCAGCTGGTGCAGTC-3 (SEQ. ID. NO: 14)'] and a heavy chain reverse primer [NATJH-ALL: 5'-GAGGAG-GCTAGCTGAGGAGACGGTGA-3 (SEQ. ID. NO: 15)'], 5 ul of 10× buffer, 1 ul of 10 mM dNTP mix, 0.5 ul of pfu DNA polymerase (Solgent, 2.5 U/ul), and distilled water. PCR program was as shown in Table 4. Another colony PCR was performed (iCycler iQ, BIO-RAD) to obtain the light chain using 1 ul of monoclonal DNA, 10 pmole/ul of a light chain forward primer [NATVK6: 5'-TTGGTGGCCACAGCGGC-CGATGTCCACTCGGACATCCAGATGAC-CCAGTCTCC-3 (SEQ. ID. NO: 16)'] and a light chain reverse primer [NATJK-CD910E4: 5'-GAG-GAGAGATCTTTTGATATCCACTTTGGT-3 (SEQ. ID. NO: 17)'], 5 ul of 10× buffer, 1 ul of 10 mM dNTP mix, 0.5 ul of pfu DNA polymerase (Solgent, 2.5 U/ul), and distilled water. PCR program was as shown in Table 4. As a result, the heavy chain and the light chain were prepared and these chains and vector were digested with restriction enzymes.

The heavy chain was reacted in the mixture comprising 15 ul of PCR gel elution product, 5 ug of pNATAB H vector, 3 ul of 10× buffer, 1 ul of NheI (Enzynomix, 10 U/ul), and distilled water at 37° C. for 2 hours. After adding 1 ul of SfiI (NEB, 20 U/ul) thereto, the mixture was further reacted at 50° C. for 2 hours. DNA of each vector and the heavy chain were eluted by using DNA-gel elution kit (Qiagen, ND). To induce ligation, the mixture composed of 1 ul of vector (10 ng), 15 ul of the heavy chain (100-200 ng), 2 ul of 10× buffer, 1 ul of ligase (1 U/ul), and distilled water stood at room temperature for 1-2 hours, to which competent cells (XL1-blue) were added. Then, the mixture stood in ice for 30 minutes, followed by heat-shock at 42° C. for 90 seconds. After the heat-shock, the mixture was placed in ice again for 5 minutes, to which 1 ml of LB medium was added. After culturing at 37° C. for 1 hour, the cells were spreaded on LB Amp plate, followed by culture at 37° C. for 16 hours.

The light chain was reacted in the mixture comprising 15 ul of PCR gel elution product, 5 ug of pNATAB L vector, 3 ul of 10× buffer, 1 ul of BglII (Enzynomix, 10 U/ul), and distilled water at 37° C. for 2 hours. After adding 1 ul of SfiI (NEB, 20 U/ul) thereto, the mixture was further reacted at 50° C. for 2 hours. DNA of each vector and the heavy chain were eluted by using DNA-gel elution kit (Qiagen, ND). To induce ligation, the mixture composed of 1 ul of vector (10 ng), 15 ul of the light chain (100-200 ng), 2 ul of 10× buffer, 1 ul of ligase (1 U/ul), and distilled water stood at room temperature for 1-2 hours, to which competent cells (XL1-blue) were added. Then, the mixture stood in ice for 30 minutes, followed by heat-shock at 42° C. for 90 seconds. After the heat-shock, the mixture was placed in ice again for 5 minutes, to which 1 ml of LB medium was added. After culturing at 37° C. for 1 hour, the cells were spread on LB Amp plate, followed by culture at 37° C. for 16 hours.

The obtained colony was inoculated in 5 ml of LB Amp medium, followed by culture at 37° C. for 16 hours, followed by DNA-prep using DNA-prep kit. Sequencing of the obtained DNA was performed using CMV-proF primer (Solgent, Korea). As a result, it was confirmed that the heavy chain and the light chain sequences of whole IgG converted from 10E4 clone were identical.

To transfect 293E cells, the heavy chain and the light chain of whole IgG converted from 10E4 clone were cultured in 100 ml of LB Amp medium, and then DNA was obtained using MiDi-prep kit. 40 ug of PEI, 10 ug of the whole CD9 10E4 heavy chain DNA, and 10 ug of the light chain DNA were added to 293 cells, followed by co-transfection. The obtained supernatant proceeded to Western blotting to investigate whether expression and combination were successfully regulated. As a result, as shown in FIG. 10, 10E4 was converted into whole IgG form, compared with the control (normal human IgG, Jackson Lab) (FIG. 10). As shown in FIG. 11, 10E4 converted by FACS also demonstrated CD9-specific binding capacity (FIG. 11).

EXPERIMENTAL EXAMPLE 1

Effect of 10E4 Human Antibody on Invasion and Migration of Ovarian Cancer Cell Line <1-1> 2774 Cell Invasion The present inventors harvested cells by using trypsin (Gibco 25300) and then the cells were washed twice with RPMI invasion medium (RPMI, 10 mM HEPES, 0.5% BSA). The cells were resuspended in the invasion medium at the density of $2 \times 10^6$/ml. Purified 10E4 antibody was diluted in the invasion medium at the concentrations of 1000 and 2000 ng/50 ul. 50 ul of the cell suspension and 50 ul of the 10E4 antibody solution were mixed, followed by pre-incubation at 37° C. for 2 hours. A 24-well transwell plate (8 um pore size, Costar 3422) was coated with matrigel (BD 354234) diluted in serum-free medium (RPMI, 10 mM HEPES) at the concentration of 1 mg/ml on the top surface of insert for 1 hour. One hour later, the matrigel remaining on the insert was eliminated and the plate was washed with serum-free medium once. 600 ul of PRMI invasion medium supplemented with 5% FBS was added to the chamber. The insert was added to the chamber containing culture medium using sterilized forceps. 100 ul of the pre-incubated cell-antibody mixture was loaded in the insert, followed by culture in a 37° C./5% $CO_2$ incubator for 24 hours. To measure the invaded cells passed through matrigel, the top side of the insert was cleaned with swab soaked with PBS. Then, the insert was placed in the chamber containing 500 ul of 3.7% paraformaldehyde (Sigma HT50), followed by fixation at room temperature for 30 minutes. After staining with 500 ul of 1% crystal violet (Sigma C3886)/100 mM NaBorate (Sigma 59640) for 30 minutes, the insert was washed with water and dried, followed by counting the cells under microscope (×100).

As a result, as shown in FIG. 12, the purified 10E4 antibody significantly inhibited invasion of 2774 (ovarian adenocarcinoma cell line) cells, compared with the control human normal IgG (FIG. 12).

<1-2> 2774 Cell Migration

The present inventors harvested 2774 (ovarian adenocarcinoma cell line) cells by using trypsin and then the cells were washed twice with RPMI migration medium (RPMI, 10 mM HEPES, 0.5% BSA). The cells were resuspended in the migration medium at the density of $8 \times 10^5$/ml. Purified 10E4 antibody was diluted in the migration medium at the concentration of 1000 ng/50 ul. 50 ul of the cell suspension and 50 ul of the 10E4 antibody solution were mixed, followed by pre-incubation at 37° C. for 2 hours. A 24-well transwell plate was coated with 0.05% gelatin (Sigma G1393) at the concentration of 1 mg/ml on the bottom side of the insert at room temperature for 1 hour. One hour later, the gelatin remaining on the insert was eliminated and the plate was washed with PBS once. 600 ul of PRMI migration medium supplemented with 5% FBS was added to the chamber. The insert was added to the chamber using sterilized forceps. 100 ul of the pre-incubated cell-antibody mixture was loaded in the insert, followed by culture in a 37° C./5% $CO_2$ incubator for 24 hours. To measure the cell migration, the top side of the insert was cleaned with swab soaked with PBS. Then, the insert was placed in the chamber containing 500 ul of 3.7% paraformaldehyde, followed by fixation at room temperature for 30 minutes. After staining with 500 ul of 1% crystal violet/100 mM NaBorate for 30 minutes, the insert was washed with water and dried, followed by counting the cells under microscope (×100).

As a result, as shown in FIG. 13, the purified 10E4 antibody significantly inhibited (3 times greater) migration of 2774 (ovarian adenocarcinoma cell line) cells, compared with the control human normal IgG (FIG. 13).

<1-3> 2774 Cell Proliferation

The present inventors harvested cells by using trypsin and then the cells were washed twice with RPMI supplemented with 2% FBS. The cells were resuspended in serum-free medium at the density of $2\times10^5$/ml. Purified 10E4 antibody was diluted in the serum-free medium at the concentrations of 250, 500 and 1000 ng/40 ul. 50 ul of the cell suspension and 40 ul of the 10E4 antibody solution were mixed, followed by pre-incubation at 37° C. for 2 hours. 10 ul of FBS was added to the cell-antibody mixture finished the reaction, which was distributed in a 96-well plate by 100 ul/well, followed by culture in a 37° C./5% $CO_2$ incubator for 24, 48 and 72 hours. 10 ul of PreMix WST-1 cell proliferation solution (Takara, MK400) was added at each time point, followed by reaction at 37° C. for 2 hours. Then, $OD_{440}$ was measured using VERSA max microplate reader.

As a result, the purified 10E4 antibody significantly inhibited, at least 30%, proliferation of 2774 cells (FIG. 14).

EXPERIMENTAL EXAMPLE 2

Identification of Epitope of CD9-ECL2 Domain Recognized by Human Antibody 10E4

<2-1> Generation of CD9-ECL2 Mutants

For the cloning of ECL2 domain alone, PCR was performed using the following primers. Each mutant was constructed based on rat sequences having homology with human sequences. Particularly, human CD9 ECL2 domain (GenBank Accession Number NP001760) was compared with corresponding Norway Rat (*Rattus norvegicus*) CD9 ECL2 domain (GenBank Accession Number NP444177) and different regions were named mutation 1, mutation 2, mutation 3 and mutation 4. PCR was performed with the forward primers F602 F [5'-CAGGGGGCCGTGGGGGCCTCCCA-CAAGGATGAGGTGAT-3 (SEQ. ID. NO: 18)'], F602 M1 [5'-TCCCACAAGGATGAGGTGATTAAG-GAACTCCAGGAGTTTTACAAGGACACCTAC-3 (SEQ. ID. NO: 19)'] and F602 M2 [5'-TTTTACAAGGACAC-CTACCAAAAGCTGAGAAACAAGGATGAGC-3 (SEQ. ID. NO: 20)'] and the reverse primers F602 M3 [5'-CT-GAGATAAACTGTTCCACGCCCCCAGC-GATACCACAGCAGTTCAACGCCATGTGGA TGGC-3 (SEQ. ID. NO: 21)'], F602 M4 [5'-GGACTTCACTTG-GAAGGATTCGAGTACTTGCTTCT-TGGGGCAGATGTCTGAGATAAA CTGTTCCA-3 (SEQ. ID. NO: 22)'], F602 M5 [5'-GATGTGGAATTTACGTG-GAAGACCTCATCGATGGCATCAGGACAG-GACTTCACTTGG AAGGA-3 (SEQ. ID. NO: 23)'], F602 M6 [5'-TAGCGGCCGACGCGGCCAAGATGTG-GAATTTACTGTGGAAGACCTCATCGATGGCA-3 (SEQ. ID. NO: 24)'], and F602 R [5'-TAGCGGC-CGACGCGGCCAA GATGTGGAATTTATTGTCGA-3 (SEQ. ID. NO: 25)'] under the same conditions shown in Table 7 (1-4). Particularly, PCR was performed with the total reaction volume of 50 ul comprising 10 pmol of each primer, 0.5 ul of pfu DNA polymerase (2.5 unit/ul) as follows; pre-denaturation at 94° C. for 2 minutes, denaturation at 94° C. for 30 seconds, annealing at 59° C. for 30 seconds, polymerization at 72° C. for 30 seconds, 30 cycles from denaturation to polymerization, and final extension at 72° C. for 10 minutes. The PCR product was digested with Sfi I, which was inserted into pYK His only vector. As a result, pYK His Only-CD9-ECL2 & CD9-ECL2 mutant plasmid comprising CMV I.E enhancer/promoter, reader sequence, CD9-ECL2 gene, Myc and 8× His tag in that order was constructed.

TABLE 7

| Mutation type | PCR number | PCR primer F | PCR primer R | Template |
|---|---|---|---|---|
| M1 | 1 | F602 F | F602 M6 | pYW600 100 ng |
| M2 | 1 | F602 F | F602 M5 | pYW600 100 ng |
|  | 2 | F602 F | F602 M6 | M2 1st PCR product 1 ul |
| M3 | 1 | F602 F | F602 M3 | pYW600 100 ng |
|  | 2 | F602 F | F602 M4 | M3 1st PCR product 1 ul |
|  | 3 | F602 F | F602 M5 | M3 2nd PCR product 1 ul |
|  | 4 | F602 F | F602 M6 | M3 3rd PCR product 1 ul |
| M4 | 1 | F602 M2 | F602 R | pYW600 100 ng |
|  | 2 | F602 M1 | F602 R | M4 1st PCR product 1 ul |
|  | 3 | F602 F | F602 R | M4 2nd PCR product 1 ul |
| Rat. CD9-ECL2 | 1 | F602 M2 | F602 M3 | pYW600 100 ng |
|  | 2 | F602 M2 | F602 M4 | Rat. CD91st PCR product 1 ul |
|  | 3 | F602 M1 | F602 M5 | Rat. CD9 2nd PCR product 1 ul |
|  | 4 | F602 F | F602 M6 | Rat. CD9 3rd PCR product 1 ul |

Primer dimers were eliminated from the PCR product using PCR purification kit (Solgent, Cat. No. SPP02-C200). First, PCRB buffer was added to the PCR product 5 times the total volume of the product, which was then well mixed and transferred in spin column, followed by centrifugation at 12,000 rpm for 30 seconds. The solution flowed down the collection tube, bottom of the column, was discarded. Then, the column was re-loaded in the collection tube, to which 750 ul of WB buffer was added, followed by centrifugation (12,000 rpm, 30 sec). The solution collected in the collection tube was discarded and centrifugation continued for 2 more minutes to eliminate the WB buffer completely. The spin column was transferred into a 1.5 ml sterilized microtube, to which 35 ul of sterilized distilled water was added. The mixture stood at room temperature for 1 minute, followed by centrifugation at 12,000 rpm for 2 minutes to obtain purified PCR product.

2 ul of Sfi I (NEB Cat. No. R0123L, 20 unit/ul), 3 ul of 10× buffer, and 15 ul of sterilized distilled water was added to 10 ul of the purified PCR product, followed by reaction at 50° C. for 2 hours. Upon completion of the reaction, the sample was electrophoresed on 1% agarose gel (50 volt, 1 hour) and stained with EtBr. Equal sized bands were cut out by using hand UV detector. Gel purification was performed by using gel extraction kit (Qiagen Cat. No. 28706). The cut out gel was placed in a sterilized microtube and weighed. QG buffer was added thereto three times the volume, followed by dissolving at 50° C. for 10 minutes. When the gel was completely dissolved, same volume of isopropanol was added thereto, which was loaded in Qiaquick spin column, followed by centrifugation at 12,000 rpm for 30 seconds. The solution down-flowed was discarded. Then, 750 ul of PE buffer was added thereto, followed by centrifugation (12,000 rpm, 30 sec). The solution collected in the collection tube was discarded and centrifugation continued for 2 more minutes to eliminate the PE buffer completely. The spin column was transferred into a 1.5 ml sterilized microtube, to which 20 ul of sterilized distilled water was added. The mixture stood at room temperature for 1 minute, followed by centrifugation at 12,000 rpm for 2 minutes to obtain purified Sfi I digestion product.

1 ul of 10× ligation buffer, 1 ul of pYW 600 Sfi I digestion product (20 ng/ul), 2 ul of sterilized distilled water, and 1 ul of ligase (Roche Cat. No. 10 716 359001. 1 unit/ul) were added to 5 ul of the Sfi I digestion product to make the total volume to be 10 ul, followed by ligation at room temperature for 1 hour. 10 ul of the ligation mixture was mixed with 100 ul of XL1-blue. The mixture was reacted in ice for 10 minutes, followed by heat shock at 42° C. for 1 minute and 30 seconds. Then, the mixture was put in ice again for 5 minutes. 900 ul of LB medium was added thereto, followed by re-generation at 37° C. for 1 hour. Centrifugation was performed at 12,000 rpm for 30 seconds. Total cells were spread on LB-Amp plate. On the next day, colonies were confirmed and then mini-prep was performed. The prepared transformed cells were cultured in 2 ml of LB-Amp medium, and then transferred into a 1.8 ml microtube, followed by centrifugation at 12,000 rpm for 30 seconds to make the cells down. Mini prep was performed with those cells by using mini-prep kit. The cells were resuspended in 250 ul of cell resuspension solution, to which 250 ul of cell lysis buffer was added, followed by inverting five times. After standing at room temperature for 1 minute, 350 ul of neutralizing buffer was added thereto, followed by inverting 5 times again. The reactant was centrifuged at 12,000 rpm for 10 minutes at 4° C. to down the tangled protein. The supernatant was transferred in spin column, followed by centrifugation at 12,000 rpm for 30 seconds. The solution downflowed was discarded. Then, 750 ul of washing buffer was added thereto, followed by centrifugation (12,000 rpm, 30 sec). The solution collected in the collection tube was discarded and centrifugation continued for 2 more minutes to eliminate the washing buffer completely. The spin column was transferred into a 1.5 ml sterilized microtube, to which 50 ul of sterilized distilled water was added. The mixture stood at room temperature for 1 minute, followed by centrifugation at 12,000 rpm for 2 minutes. The obtained mini-prep product was digested with Sfi I by 5 ul each and cloning was confirmed. Then, mutant sequences were confirmed by sequencing.

TABLE 8

| Type | Sequence | SEQ. ID. NO |
|---|---|---|
| p-Myc-His CD9-ECL2 wild type | MGWSYIILFLVATATDVHSQGAV GASHKDEVIKEVQEFYKDTYNKL KTKDEPQRETLKAIHYALNCCGL AGGVEQFISDICPKKDVLETFTV KSCPDAIKEVFDNKFHILAASAE QKLISEEDLNSAVDHHHHHHHH | SEQ. ID. NO: 26 |
| CD9-ECL2 | SHKDEVIKEVQEFYKDTYNKLK TKDEPQRETLKAIHYALNCCGL AGGVEQFISDICPKKDVLETFTV KSCPDAIKEVFDNKFHI | SEQ. ID. NO: 27 |
| M1 | SHKDEVIKEVQEFYKDTYNKLK TKDEPQRETLKAIHYALNCCGL AGGVEQFISDICPKKDVLETFTV KSCPDAIDEVFHSKFHI | SEQ. ID. NO: 28 |
| M2 | SHKDEVIKEVQEFYKDTYNKLK TKDEPQRETLKAIHYALNCCGL AGGVEQFISDICPKKQVLESFQV KSCPDAIDEVFHSKFHI | SEQ. ID. NO: 29 |
| M3 | SHKDEVIKEVQEFYKDTYNKLKT KDEPQRETLKAIHMALNCCGIAG GVEQFISDICPKKQVLESFQVKSC PDAIDEVFHSKFHI | SEQ. ID. NO: 30 |

TABLE 8-continued

| Type | Sequence | SEQ. ID. NO |
|---|---|---|
| M3B | SHKDEVIKEVQEFYKDTYNKLKT KDEPQRETLKAIHMALNCCGIAG GVVQFISDICPKKQVLESFQVKSC PDAIDEVFHSKFHI | SEQ. ID. NO: 31 |
| M4 | SHKDEVIKELQEFYKDTYQKLRN KDEPQRETLKAIHYALNCCGLAG GVEQFISDICPKKDVLETFTVKSC PDAIKEVFDNKFHI | SEQ. ID. NO: 32 |
| R5 | SHKDEVIKELQAFYKDTYQKLRN KDEPQRETLKAILMALNCCGIAG GVEQFISDICPKKQVLESFQVKSC PDAIDEVFPSKFHI | SEQ. ID. NO: 33 |
| R6 | SHKDEVIKELQEFYKDTYQKLRN KDEPQRETLKAIHMALNCCGIAG GVEQFISDICPKKQVLESFQVKSC PDAIDEVFHSKFHI | SEQ. ID. NO: 34 |
| R-2B | SHKDEVIKEVQEFYKDTYQKRRN KDEPQRETLKAIHMALNCCGIAG GVEQFISDICPKKQVLESFQVKSC PDAIDEVFHSKFHI | SEQ. ID. NO: 35 |

<2-2> Preparation of CD9-ECL2 Mutant Protein

The present inventors distributed 293E cells on 100 mm dish at the density of $5 \times 10^6$ cells/150 mm dish, followed by culture in a 37° C. $CO_2$ incubator for 16-20 hours. When cell confluency reached 70-80%, transfection was performed. For the transfection, 10 ug of CD9-ECL2 DNA mutant and 20 ug of PEI (polyethylenimine M.W~25,000, Polysciences, Inc. Cat. No. 23966, 2 mg/ml) were mixed in DMEM (Dulbecco's Modified Eagle's Medium, Biowhittaker (Lonza) Cat. No, 12-604F, No FBS), which stood at room temperature for 20 minutes. 20 minutes later, the mixture was dropped on the plate covered with 293E cells, followed by shaking well. On the next day, the cells were washed, to which DMEM (No FBS) was added. Supernatant was obtained every 2-3 days. The supernatants obtained on day 2, day 5 and day 7 proceeded to Western blotting.

Each supernatant was loaded by 24 ul at 100 V for 2 hours, and then transferred to NC membrane (Millipore Cat. No. HATF00010) at 85V for 2 hours. The membrane finished with transfer was blocked by using blocking buffer (4% skim milk in TEST) at room temperature for 1 hour. A-His-HRP (Sigma, Cat. No. A7058) was diluted with blocking buffer (4% skim milk in TBST) at 1:4000 and binding was induced at room temperature for 1 hour. The membrane was washed with TBST 5 times every 10 minutes, followed by development (Intron, Cat. No. 12145). Expression of each mutant was confirmed by Western blotting (FIG. 15). Based on that, epitopes of ALB6 and 10E4 were confirmed by ELISA. A 96-well immuno-plate (NUNC) was coated with coating buffer comprising ALB6 and 10E4 (100 ng/100 ul/well each) at 4° C. for 16 hours, followed by blocking with 4% PBST (skim milk dissolved in 1× PBS) for 2 hours. Each well of the 96-well immuno-plate was washed three times with 0.2 ml of PBST (PBS-tween20 (0.05%)). From the supernatants obtained on day 5 confirmed to contain a large number of mutants confirmed by Western blotting, wild type, M1 and M4 supernatants were selected. 100 ul of the selected supernatant was added to each well of the plate, followed by reaction for 2 hours. The plate was washed again. The secondary antibody anti-His-HRP (Sigma A7058) was diluted at 1:1000, followed by reaction at room temperature for 30 minutes. Washing was performed three times by the same manner as described above. OPD tablet (Sigma 8787-TAB) was added to PC buffer [$C_6H_8O_7H_2O$ (Sigma, C0706) 5.1 g, $Na_2HPO_4$ (Sigma, 57907 7.3 g)] to make substrate solution, which was added to each well by 100 ul/well, followed by color development for 10 minutes. Color development was terminated by adding 2 M $H_2SO_4$ solution. Then, $OD_{490}$ was measured by using ELISA reader (Molecular Device).

As a result, 10E4 antibody demonstrated weak binding to M1 (186K→D, 190D→H and 191N→S) among many mutant forms of CD9-ECL2. However, unlike 10E4, ALB6 demonstrated strong binding to M1 (Table 9). In the meantime, both 10E4 and ALB6 demonstrated strong binding to M4. So, ABL6 and 10E4 recognize different epitopes when they recognize CD9, the ovarian cancer target antigen. And 10E4 recognizes the peptide fragment represented by SEQ. ID. NO: 36 (KEVFDN) in CD9-ECL2 as an epitope.

TABLE 9

|  | ABL-6 | | nor mouse IgG | | | 10E4 | normal human IgG |
| --- | --- | --- | --- | --- | --- | --- | --- |
| M1 | 0.334 | 0.383 | 0.046 | 0.056 | M1 | 0.084 | 0.054 |
| M4 | 0.485 | 0.574 | 0.04 | 0.047 | M4 | 0.398 | 0.053 |
| Wild type | 0.427 | 0.506 | 0.044 | 0.053 | Wild type | 0.375 | 0.056 |
| mock sup | 0.04 | 0.051 | 0.042 | 0.048 | mock sup | 0.045 | 0.054 |

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

The invention claimed is:

1. A purified CD9-specific human antibody or antigen binding fragment thereof, comprising a heavy chain containing:
   a heavy chain variable region (VH) comprising HCDR1 having the amino acid sequence of SEQ ID NO: 7, HCDR2 having the amino acid sequence of SEQ ID NO: 8, and HCDR3 having the amino acid sequence of SEQ ID NO: 9; and
   a light chain containing light chain variable region (VL) comprising LCDR1 having the amino acid sequence of SEQ ID NO: 11, LCDR2 having the amino acid of SEQ ID NO: 12, and LCDR3 having the amino acid sequence of SEQ ID NO: 13.

2. The purified human antibody according to claim 1, wherein the antibody recognizes the peptide fragment represented by SEQ ID NO: 36 in CD9 extracellular loop 2 domain (CD9-ECL2) as an epitope.

3. A method for producing a CD9-specific human antibody comprising the following steps:
   1) culturing a transformant generated by simultaneously introducing an expression vector containing a gene encoding the heavy chain of the human antibody of claim 1 and an expression vector containing the gene encoding the light chain of the human antibody of claim 1, into a host cell in culture;
   2) culturing said host cell under conditions suitable to allow expression of the human antibody; and
   3) purifying the antibody of claim 1 from the culture solution of step 1.

4. A method for treating ovarian cancer overexpressing CD9 containing the step of administering a pharmaceutically effective dose of the purified human antibody of claim 1 to a subject with ovarian cancer.

5. A method for immunodetection of cancer overexpressing CD9 in vitro containing the step of contacting cancer cells with the purified human antibody of claim 1.

6. The antigen binding fragment of the purified CD9-specific human antibody of claim 1, wherein the antigen binding fragment has CD9 neutralizing effect, and wherein the antigen binding fragment is selected from the group consisting of: Fab, Fd, Fv, dAb, F(ab')$_2$, scFv, scFv dimer, and diabody.

7. The purified CD9-specific human antibody of claim 1, comprising a heavy chain containing:
   a heavy chain variable region (VH) comprising HCDR1 having the amino acid sequence set forth as SEQ ID NO: 7, HCDR2 having the amino acid sequence set forth as SEQ ID NO: 8, and HCDR3 having the amino acid sequence set forth as SEQ ID NO: 9; and
   a light chain containing light chain variable region (VL) comprising LCDR1 having the amino acid sequence set forth as SEQ ID NO: 11, LCDR2 having the amino acid sequence set forth as SEQ ID NO: 12, and LCDR3 having the amino acid sequence set forth as SEQ ID NO: 13.

* * * * *